(12) United States Patent
Andersen et al.

(10) Patent No.: US 7,410,951 B2
(45) Date of Patent: Aug. 12, 2008

(54) BIOLOGICALLY ACTIVE PEPTIDES AND COMPOSITIONS, THEIR USE

(75) Inventors: Raymond Andersen, Vancouver (CA); John Coleman, Vancouver (CA); Dilip De Silva, Vancouver (CA); Fangming Kong, Vancouver (CA); Edward Piers, Vancouver (CA); Debra Wallace, Vancouver (CA); Michel Roberge, Vancouver (CA); Theresa Allen, Edmonton (CA)

(73) Assignee: The University of British Columbia, Vancouver (CA)

( * ) Notice: Subject to any disclaimer, the term of this patent is extended or adjusted under 35 U.S.C. 154(b) by 0 days.

(21) Appl. No.: 11/034,922

(22) Filed: Jan. 14, 2005

(65) Prior Publication Data

US 2005/0171137 A1    Aug. 4, 2005

Related U.S. Application Data

(62) Division of application No. 09/593,417, filed on Jun. 14, 2000, now Pat. No. 6,870,028, which is a division of application No. 08/930,584, filed as application No. PCT/GB96/00942 on Apr. 22, 1996, now Pat. No. 6,153,590.

(30) Foreign Application Priority Data

Apr. 20, 1995 (GB) .................................. 9508195.6

(51) Int. Cl.
*C07K 5/06* (2006.01)
(52) U.S. Cl. ........................ 514/19; 514/18; 514/411; 530/331
(58) Field of Classification Search ................ 514/411, 514/18, 19; 530/331
See application file for complete search history.

(56) References Cited

U.S. PATENT DOCUMENTS

| | | | |
|---|---|---|---|
| 4,285,935 A | | 8/1981 | Etschenberg et al. |
| 4,371,536 A | * | 2/1983 | Braestrup et al. ........... 514/292 |
| 5,081,225 A | | 1/1992 | O'Sullivan et al. |
| 5,340,802 A | * | 8/1994 | Shiosaki et al. ............... 514/18 |
| 5,356,794 A | | 10/1994 | Fromageot et al. |
| 5,661,175 A | | 8/1997 | Kashman et al. |
| 5,721,250 A | | 2/1998 | Morriello et al. |
| 5,736,517 A | | 4/1998 | Bogden et al. |
| 7,064,211 B2 | * | 6/2006 | Kowalczyk et al. ......... 546/189 |

FOREIGN PATENT DOCUMENTS

NZ    216551    9/1989
NZ    224706    7/1990
WO    93/17701    *    9/2006

OTHER PUBLICATIONS

Lippke K.P., (Archiv der Pharmazie 320(2), 145-153, 1987).*
Shintaro, Inoue (Analytical Biochemistry 132(2) 468-80, 1983).*
Baeza, Claudio Rivera (Acta Chemica Scandinavica 48(5), 434-8, 1994).*
Chan et al., "Stereostructures of Geodiamolides A and B, Novel Cyclodepsipeptides from the Marine Sponge *Geodia* sp.," J. Org. Chem., 1987, vol. 52, No. 14, pp. 3091-3093.
Coleman et al., "Cytotoxic Peptides from the Marine Sponge *Cymbastela* sp.," Tetrahedron, 1995, vol. 51, No. 39, pp. 10653-10662.
Coleman et al., "Hemiasterlin Methyl Ester," Acta Cryst., 1996, C52, pp. 1525-1527.
Crews et al., "Milnamide A, an Unusual Cytotoxic Tripeptide from the Marine Sponge *Auletta cf. constricta*," J. Org. Chem., 1994, vol. 59, No. 11, pp. 2932-2934.
Fabian et al., "Growth Modulation and Differentiation of Acute Myeloid Leukemia Cells by Jaspamide," Experimental Hematology, 1995, vol. 23, No. 7, pp. 583-587.
Huang et al., "Main Chain and Side Chain Chiral Methylated Somatostatin Analogs: Syntheses and Conformational Analyses," J. Am. Chem. Soc., 1992, vol. 114, No. 24, pp. 9390-9401.
Minaev et al., "Fluorescence Study of A-128-OP Antibiotic," Viniti Deposited Publication, 1977, 2778-77, pp. 1-14.
Minaev et al., "Fluorescence Study of A-128-OP Antibiotic," Chemical Abstracts, 1979, vol. 91, p. 710.
Talpir et al., "Hemiasterlin and Geodiamolide TA; Two New Cytotoxic Peptides from the Marine Sponge Hemiasterella Minor (Kirkpatrick)," Tetrahedron Letters, 1994, vol. 35, No. 25, pp. 4453-4456.
Hungarian Search Report for corresponding Hungarian Application No. P0105460 in English, Jul. 2002.
Hungarian Abstract of document cited in Hungarian Search Report (C9)—HU P9900728 A, Aug. 1999.

* cited by examiner

*Primary Examiner*—David Lukton
(74) *Attorney, Agent, or Firm*—Arent Fox LLP

(57) ABSTRACT

Derivatives of hemiasterlin or Geodiamolide G having antimitotic activities and useful in treating cancer. These derivatives are represented by formula I

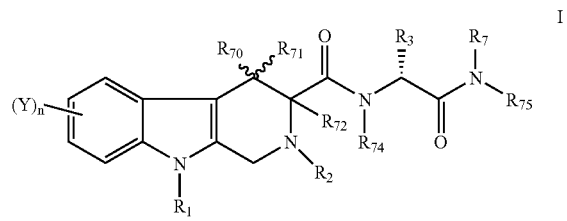

wherein Y, n, $R_1$, $R_2$, $R_3$, $R_7$, $R_{70}$, $R_{71}$, $R_{72}$, $R_{74}$, and $R_{75}$ are as defined in the specification.

11 Claims, 1 Drawing Sheet

Comparison of antimitotic activity of Hemiasterlins with that of known antimitotic agents.

Antimitotic activity of chemically modified Hemiasterlin.

US 7,410,951 B2

BIOLOGICALLY ACTIVE PEPTIDES AND COMPOSITIONS, THEIR USE

CROSS-REFERENCE TO RELATED APPLICATIONS

This is a divisional of U.S. patent application Ser. No. 09/593,417, filed Jun. 14, 2000, now U.S. Pat. No. 6,870,028 which is a divisional of U.S. patent application Ser. No. 08/930,584, filed Feb. 2, 1998, now U.S. Pat. No. 6,153,590, issued Nov. 28, 2000, which in turn is the U.S. National Stage of PCT/GB96/00942, filed Apr. 22, 1996. The disclosures of all prior applications are hereby incorporated herein in their entirety by reference.

This invention relates to novel biologically active compounds and compositions, their use and derivation.

The invention has involved the extraction of novel biologically active compounds from marine sponges.

Except where otherwise stated, throughout this specification, any alkyl moiety suitably has up to 8, especially up to 6, most preferably up to 4, carbon atoms and may be of straight chain or, where possible, of branched chain structure. Generally, methyl is a preferred alkyl group. Halogen atoms may be fluorine, chlorine, bromine or iodine. A preferred acyl group is alkylcarbonyl, especially acetyl.

Except where otherwise stated in this specification, optional substituents of an alkyl group may include halogen atoms, for example fluorine, chlorine, bromine and iodine atoms, and nitro, cyano, alkoxy, hydroxy, amino, alkylamino, sulphinyl, alkylsulphinyl, sulphonyl, alkylsulphonyl, amido, alkylamido, alkoxycarbonyl, haloalkoxycarbonyl and haloalkyl groups. Preferably, optionally substituted alkyl groups are unsubstituted.

Except where otherwise stated, throughout this specification the recitation of a compound denotes all possible isomers possible within the structural formula given for those compounds, in particular geometrical and optical isomers. Unless otherwise stated definitions are to be regarded as covering mixtures of isomers, and individual isomers, including racemic mixtures, where they can be resolved.

Except if otherwise stated, definitions of compounds in this specification are to be regarded as covering all possible salts of the compounds.

Compounds according to the first aspect of the invention have been found to be surprisingly effective in the in vivo treatment of cancer.

In accordance with the first aspect of the present invention there is provided the use of a hemiasterlin compound of general formula

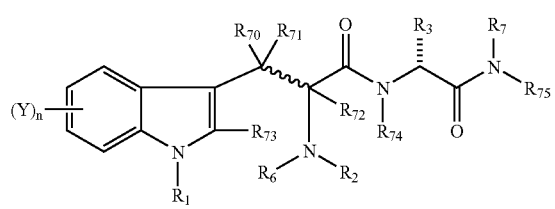

I wherein:
$R_1$ and $R_{70}$ independently represent a hydrogen atom or an optionally substituted alkyl or acyl group;
$R_2$ represents a hydrogen atom or an optionally substituted alkyl or acyl group or is absent when $R_6$ represents a group —CH= as hereinafter described;

$R_{73}$ represents a hydrogen atom or an optional substituent or is absent when $R_6$ represents a methylene group or a group —CH= as hereinafter described;
Y represents an optional substituent;
n represents 0, 1, 2, 3, or 4;
$R_3$ represents a hydrogen atom, or an optionally substituted alkyl group;
$R^{74}$ represents a hydrogen atom, a hydroxy group or an optionally substituted alkyl or acyl group;
$R_7$ represents a hydrogen atom or an alkyl group;
$R_{75}$ represents an optionally substituted alkyl group; and
i) $R_6$ and $R_{71}$ independently represent a hydrogen atom or an optionally substituted alkyl or acyl group; and
$R_{72}$ represents a hydrogen atom;
or
ii) $R_{71}$ represents a hydrogen atom or an optionally substituted alkyl or acyl group and $R_{72}$ represents a hydrogen atom or $R_{71}$ and $R_{72}$ each represent radicals so that a double bond is formed between the carbon atoms to which they are attached; and
$R_6$ represents an optionally substituted methylene group bonded to the indole moiety thereby to form a tricyclic moiety; or
$R_6$ represents an optionally substituted group —CH= bonded to the indole moiety thereby to form an aromatic tricyclic moiety; for the manufacture of a medicament for use in therapy.

DETAILED DESCRIPTION OF THE INVENTION

Figure 1:
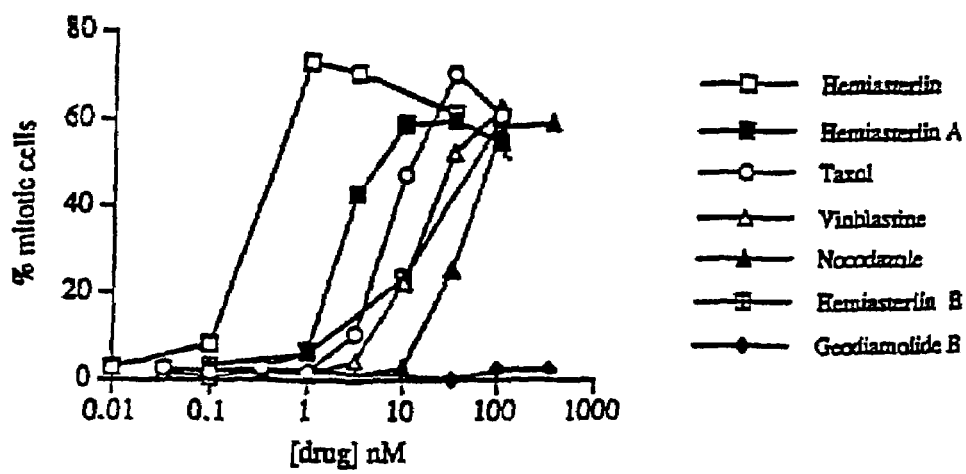
FIG. 1 shows a comparison of antimitotic activity of Hemiasterlins with that of known antimitotic agents.

Preferably, $R^1$ represents a hydrogen atom or an alkyl group, especially a methyl group. More preferably, $R_1$ represents a hydrogen atom.

Suitably, $R_2$ represents a hydrogen atom or an acyl group. An acyl group may be a benzoyl group, but is preferably an alkylcarbonyl group. An especially preferred acyl group is an acetyl group. Preferably, $R_2$ represents a hydrogen atom.

Preferably, $R_{70}$ represents a hydrogen atom or an alkyl group, especially a methyl group.

Where Y and/or $R_{73}$ represent optional substituents, said substituents may be independently selected from halogen, especially fluorine, chlorine, bromine and iodine atoms and alkyl, acyl, —OH, —O-alkyl, O-acyl, —NH$_2$, —NH-alkyl, —N(alkyl)$_2$, —NH-acyl, —NO$_2$, —SH, —S-alkyl and —S-acyl, wherein the alkyl and acyl groups of the substituents are optionally substituted.

Preferred optional substituents represented by Y and/or $R_{73}$ are alkyl groups.

Preferably, $R_{73}$ represents a hydrogen atom.

Preferably, n represents 0, 1 or 2. More preferably, n represents 0.

Suitably, $R_3$ represents an alkyl group. Preferably, $R_3$ represents a $C_{3-6}$, especially $C_{3-4}$, branched alkyl group, for example tertiary butyl or isopropyl.

Suitably, $R_{74}$ represents a hydrogen atom or methyl group, especially a hydrogen atom.

Suitably, $R_7$ represents an alkyl, preferably methyl, group.

Preferably, $R_6$ represents a hydrogen atom, or an optionally substituted alkyl group, or a methylene group bonded to the indole moiety thereby to form a tricyclic moiety. More preferably, $R_6$ represents an alkyl group.

Preferably, $R_{71}$ independently represents a hydrogen atom or an optionally substituted alkyl or acyl group. More preferably, $R_{71}$ represents an alkyl, especially a methyl group.

Preferably, $R_6$ and $R_{71}$ are as described in i) above.

$R_{75}$ may represent a group of general formula

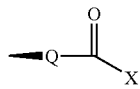

II wherein Q represents an optionally substituted —$CH_2$—, —$CH_2CH_2$—, —$CH_2CH_2CH_2$—, —$CH_2CHCH$—, —CH, C.C.— or phenylene moiety; and X represents a group —$OR_8$, —$SR_8$, or —$N_9R_{10}$ wherein $R_8$, $R_9$ and $R_{10}$ independently represent a hydrogen atom or an optionally substituted alkyl group.

Where Q represents one of the aforesaid optionally substituted acyclic moieties, the moiety may be substituted by one or more alkyl groups. A phenylene moiety may be substituted by one or more substituents Y as described above.

Where X represents a group —$OR_8$, suitably $R_8$ represents a hydrogen atom or a methyl group. Preferably, $R_8$ represents a hydrogen atom.

Where X represents a group —$NR_9R_{10}$, suitably $R_9$ represents a hydrogen atom or an alkyl group, for example a methyl group and $R_{10}$ represents a substituted alkyl group.

Where $R_{10}$ represents a substituted alkyl group, said group preferably represents a group of general formula —$CHR_{21}COOH$ wherein $R_{21}$ represents an optionally substituted alkyl group. Preferably, $R_{21}$ represents a group which includes at least one nitrogen atom. Preferably, $R_{21}$ represents a group of general formula —$(CH_2)_xNR_{22}R_{23}$ wherein x is an integer, preferably in the range 1-4, and $R_{22}$ and $R_{23}$ independently represent a hydrogen atom or an optionally substituted alkyl, alkenyl or imine group. Preferably, $R_{22}$ represents a hydrogen atom and $R_{23}$ represents an imine group —C(NH)$NH_2$.

Preferably, X represents a group —$OR_8$, wherein $R_8$ represents a hydrogen atom.

Preferably, $R_{75}$ represents a group of general formula

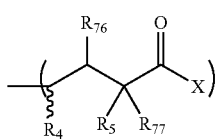

III wherein $R_4$ and $R_5$ independently represent a hydrogen atom or an optionally substituted alkyl group; $R_{76}$ and $R_{77}$ each represent a hydrogen atom or a radical so that a double bond is formed between the carbon atoms to which they are attached; and X is as described above.

It has been discovered that compounds of general formula I, can cause mitotic arrest and the production of abnormal mitotic spindles. Accordingly, the invention extends, in a second aspect, to the use of a compound of general formula I as an antimitotic compound.

The compound may be used in vivo or in vitro as an antimitotic compound in, for example, procedures that require the blocking of cells in mitosis, such as the preparation of mitotic spreads for karyotype analysis and the probing of microtubule function in mitotic cells.

In a third aspect, the invention provides a novel compound of general formula I as described herein, but excluding a single compound of general formula I wherein $R_1$ represents methyl, $R_2$ represents a hydrogen, $R_{70}$ represents methyl, $R_{71}$ represents methyl, $R_{73}$ represents hydrogen, n represents 0, $R_3$ represents t-butyl, $R_{74}$ represents hydrogen, $R_6$ represents methyl, $R_7$ represents methyl, $R_{72}$ represents hydrogen and $R_{75}$ represents —$CH(CH(CH_3)_2)CH.CCH_3.COOH$. The excluded compound is hemiasterlin.

Preferably, there is provided a compound of general formula I as described herein, but excluding a compound in which $R_1$ represents a methyl group.

Preferably, there is provided a compound of general formula I as described herein, but excluding a compound in which $R_2$ represents a hydrogen atom.

One class of preferred novel compounds comprises hemiasterlins of general formula I wherein:

$R_1$ represents a hydrogen atom;

$R_2$ represents a hydrogen atom, or an alkyl group, or an acyl group;

$R_3$ represents a hydrogen atom, or an optionally substituted alkyl group;

n represents O;

$R_{70}$ and $R_{71}$ independently represent a hydrogen atom or optionally substituted alkyl group, but preferably each represent a methyl group;

$R_{72}$, $R_{73}$ and $R_{74}$ represent hydrogen atoms;

$R_7$ represents a hydrogen atom or an alkyl group;

$R_6$ represents a hydrogen atom, or an optionally substituted alkyl group, or a methylene group bonded to the indole moiety thereby to form a tricyclic moiety;

$R_{75}$ represents a group of general formula III described above wherein $R_4$ represents a hydrogen atom, or an optionally substituted alkyl group; $R_5$ represents a hydrogen atom or an alkyl group; $R_{76}$ and $R_{77}$ represent radicals as described; and X represents a group —$OR_8$ or a group —$NR_9R_{10}$, wherein $R_8$, $R_9$ and $R_{10}$ independently represent a hydrogen atom or an optionally substituted alkyl group.

Another class of preferred novel compounds comprises hemiasterlins of general formula I wherein:

$R_1$ represents a hydrogen atom or an alkyl group;

$R_2$ represents an acyl group;

$R_3$ represents a hydrogen atom, or an optionally substituted alkyl group;

n represents O;

$R_{70}$ and $R_{71}$ independently represent a hydrogen atom or optionally substituted alkyl group, but preferably each represent a methyl group;

$R_{72}$, $R_{73}$ and $R_{74}$ represent hydrogen atoms;

$R_7$ represents a hydrogen atom or an alkyl group;

$R_6$ represents a hydrogen atom, or an optionally substituted alkyl group, or a methylene group bonded to the indole moiety thereby to form a tricyclic moiety;

$R_{75}$ represents a group of general formula III described above wherein $R_4$ represents a hydrogen atom, or an optionally substituted alkyl group; $R_5$ represents a hydrogen atom or an alkyl group; $R_{76}$ and $R_{77}$ represent radicals as described; and X represents a group —$OR_8$ or a group —$NR_9R_{10}$, wherein $R_8$, $R_9$ and $R_{10}$ independently represent a hydrogen atom or an optionally substituted alkyl group.

Another class of preferred novel compounds comprises criamides of general formula I wherein:

$R_1$ represents a hydrogen atom or an alkyl group;

$R_2$ represents a hydrogen atom, or an alkyl group, or an acyl group;

$R_3$ represents a hydrogen atom, or an optionally substituted alkyl group;

n represents O;

$R_{70}$ and $R_{71}$ independently represent a hydrogen atom or optionally substituted alkyl group, but preferably each represent a methyl group;

$R_{72}$, $R_{73}$ and $R_{74}$ represent hydrogen atoms;

$R_6$ represents a hydrogen atom, or an optionally substituted alkyl group, or a methylene group bonded to the indole moiety thereby to form a tricyclic moiety;

$R_{75}$ represents a group of general formula III described above wherein $R_4$ represents a hydrogen atom, or an optionally substituted alkyl group; $R_5$ represents a hydrogen atom or an alkyl group; $R_{76}$ and $R_{77}$ represent radicals as described; and X represents a group —$NR_9R_{10}$, wherein $R_9$ and $R_{10}$ independently represent a hydrogen atom or an optionally substituted alkyl group.

In formulas I and III drawn above, the bonds drawn in wavy line are from carbon atoms which are, or may be, optical centres.

Preferably, in the compound of general formula I the following optical configurations predominate.

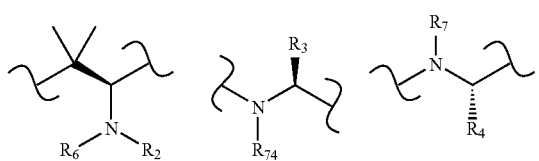

In accordance with a further aspect of the present invention there is provided a geodiamolide compound of general formula

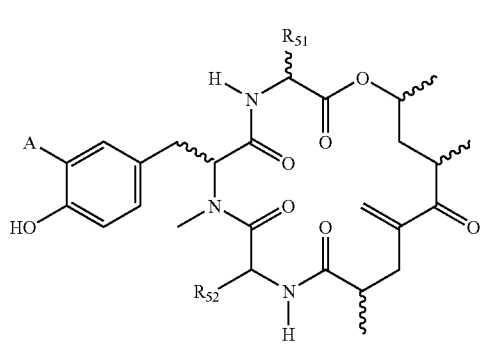

wherein:

$R_{51}$ represents an alkyl group;

$R_{52}$ represents a hydrogen atom or an alkyl group; and

A represents a halogen atom.

Preferably, $R_{51}$ represents a methyl group.

Suitably, $R_{52}$ represents a hydrogen atom or, preferably, a methyl group.

Suitably, A represents a chlorine, bromine or, preferably, an iodine atom.

In the formula IV as drawn above the bonds shown in wavy line are from carbon atoms which are optical centres, except for the carbon atoms carrying moieties $R_{51}$ and $R_{52}$, when those moieties are hydrogen atoms. Preferably, the following optical configuration predominates.

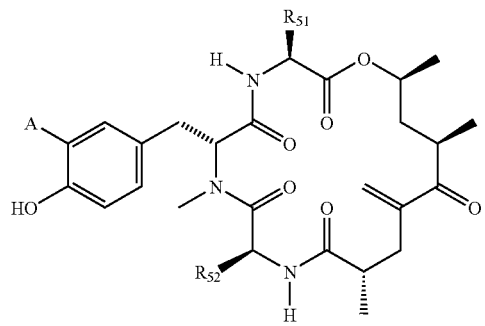

Certain compounds of the general formulae I and IV as defined above may be obtained from the marine sponge *Cymbastela* sp. (formerly classified as *Pseudaxinyssa* sp.); or be a derivatisation of compounds obtained therefrom. Derivatisation of compounds of general formula I may involve standard acylation of the extracted compounds, optionally by standard esterification. Alternatively compounds of the general formula I and IV may be prepared by entirely synthetic routes.

The invention extends to the use of a compound of general formula IV for the preparation of a medicament for use in therapy.

Compounds of general formula I may be prepared by coupling amino acid moieties A, B and C as represented below.

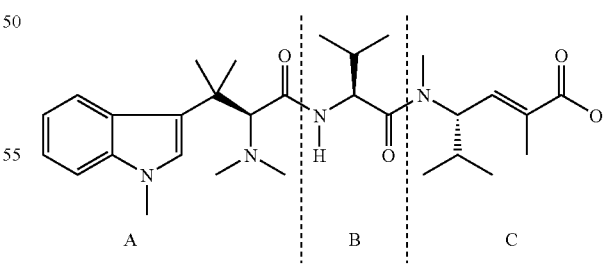

The coupling reactions may involve standard procedures. The amino acid moieties A, B, C may be prepared by standard procedures or in procedures analogous to the procedures described in the examples hereinafter.

One general procedure for the preparation of certain compounds of general formula I is provided below.

Compounds of general formula I wherein $R_{75}$ represents

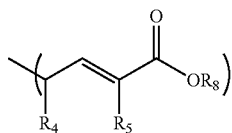

may be prepared by reacting a compound of general formula

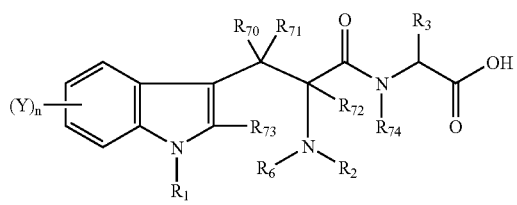

with a compound of general formula

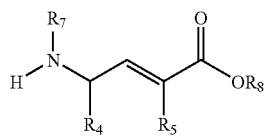

A coupling agent, for example N,N'-dicyclohexylcarbodiimide (DCC), is suitably used in the reaction. The reaction suitably comprises contacting compounds V and VI in the presence of the coupling agent, a base such as triethanolamine (TEA) and an organic solvent, such as acetonitrile, suitably at a reduced temperature. After a period of time, an inorganic base, for example sodium hydroxide may be added and, subsequently, the temperature raised to ambient temperature and trifluoroacetic acid (TFA) added. The desired compound of general formula I may then be isolated by standard techniques.

Compounds of general formula VI may be prepared by reacting a compound of general formula

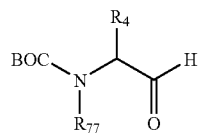

wherein BOC (tert-butoxycarbonyl) is a protecting group, with an ylid of formula for example $(Ph)_3=CR_5CO_2R_8$. The reaction is suitably carried out in the presence of potassium carbonate in a 1:1 mixture of THF/water as described in R. Lloyd (1994) Ph.D. Thesis, University of Cambridge. The protecting group BOC is suitably removed, when required, by reaction in TFA for about 2 hours at ambient temperature.

Compounds of general formula VII may be prepared by reacting a compound of general formula

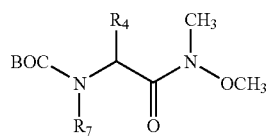

with a reducing agent, for example lithium aluminium hydride in tetrahydrofuran.

Compounds of general formula VIII may be prepared from compounds of general formula

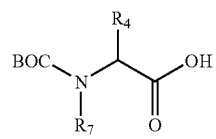

using the method described in Synthesis 1983, 676.

Compounds of general formula IX may be prepared from compounds of general formula

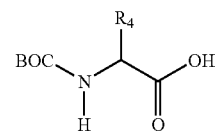

by reaction with a compound of general formula $R_7I$ in the presence of an alkali metal hydride and in THF, using the method described in Can.J.Chem. 1973, 51, 1915.

Compounds of general formula V may be prepared by reacting a compound of general formula

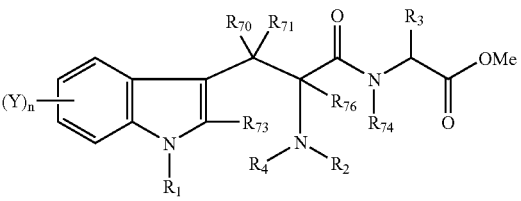

initially with a base, for example dilute sodium hydroxide solution, followed by acidification down to about pH6. In some circumstances, it is desirable to protect the group $-NR_6R_2$ from reaction and this is suitably afforded using a protecting agent such as BOC.

Compounds of general formula XI may be prepared by reacting a compound of general formula

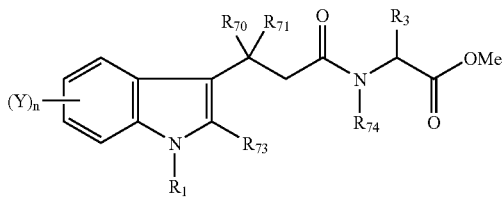

with a base followed by treatment with an azide compound. The azide derivative of compound XII may then be reduced to form an amine derivative which may then be treated with groups $R_{61}$ and/or $R_{21}$ in the presence of a base, for example sodium hydride, to afford the group $R_6R_2N$— in the compound of formula XI.

Compounds of general formula XII may be prepared by coupling compounds of general formula

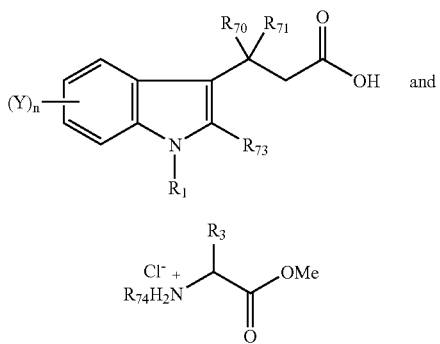

using a coupling agent, such as DCC, a base such as TEA and in an organic solvent such as acetonitrile suitably at about 0° C.

Compounds of general formula XIII may be prepared from a compound of general formula

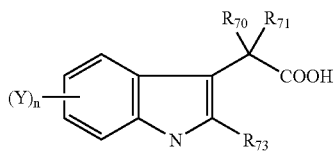

by processes well known to skilled persons in the art.

Compounds of general formula XIV and XV may be prepared by processes well known to skilled persons in the art.

Compounds of general formula I wherein $R_{75}$ represents

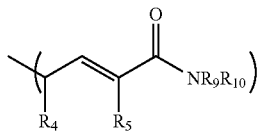

may be prepared by reacting a compound of general formula I as described above with an amine of general formula $R_9R_{10}NH$. The reaction is suitably carried out in the presence of a coupling agent such as DCC, a base such as TEA and in an organic solvent, such as acetonitrile, suitably at a reduced temperature. In certain circumstances, the group —$NR_6R_2$ may need protecting from undesired reactions and this is suitably afforded using a protecting agent such as BOC.

In accordance with a further aspect of the present invention there is provided a method of obtaining a compound of general formula I by extraction of a compound of general formula I from *Cymbastela* sp., including the steps of separation and purification; and optionally derivatising said compound to derive a further compound of general formula I.

Derivatisation of a compound of general formula I may include acylation and/or esterification steps. Esterification and/or acylation steps may be undertaken under standard conditions.

In accordance with a further aspect of the present invention there is provided a method of obtaining a compound of general formula IV by extraction of a compound of general formula IV from *Cymbastela* sp. including the steps of separation and purification; and optionally derivatising said compound to derive a further compound of general formula IV.

Compounds of the general formula I and IV are biologically active. The invention further relates to the biological use of a compound of general formula I or IV. Compounds of general formula I or IV may have pesticidal, for example insecticidal activity. Preferably, however, the use is in the veterinary or, most preferably, the pharmaceutical field.

The compounds described herein may in particular have utility as antibacterial and/or antiviral agents, and/or, especially, as cytotoxic agents.

The invention further provides the use of any compound of general formula I or IV for the manufacture of a medicament for use in the treatment of cancer or a tumor in a mammal.

In using a compound of general formula I or IV as described in any statement herein, the compound is preferably administered to a patient in a pharmaceutical or veterinary composition comprising also a pharmaceutically or veterinarily acceptable carrier, and optionally, one or more other biologically active ingredients. Such compositions may be in any form used for administering pharmaceuticals, for example any form suitable for oral, topical, vaginal, parenteral, rectal and inhalatory application. The compositions may be provided in discrete dose units. The carriers may be particulate, with the compositions being, for example, tablets or powders, or liquid, with the compositions being, for example, oral syrups or injectable liquids, or gaseous, for inhalatory application.

For oral administration an excipient and/or binder may be present. Examples are sucrose, kaolin, glycerin, starch dextrins, sodium alginate, carboxymethylcellulose and ethyl cellulose. Colouring and/or flavouring agents may be present. A coating shell may be employed. For rectal administration oleaginous bases may be employed, for example lanolin or cocoa butter. For an injectable formulation buffers, stabilisers and isotoic agents may be included.

The dosage of the compounds of general formula I and IV may depend upon the weight and physical condition of the patient; on the severity and longevity of the illness; and on the particular form of the active ingredient, the manner of administration and the composition employed. A daily dose of from about 0.001 to about 100 mg/kg of body weight taken singly or in separate doses of up to 6 times a day, or by continuous infusion, embraces the effective amounts most typically required. A preferred range is about 0.01 to about 50 mg/kg of body weight, per day, most preferably about 0.1 to about 30 mg/kg of body weight, per day.

It is to be understood that use of a compound of general formula I or IV in chemotherapy can involve such a compound being bound to an agent, for example a monoclonal or polyclonal antibody, a protein or a liposome, which assists the delivery of the said compound to tumour cells.

Therefore, the invention relates further to a pharmaceutical and veterinary composition comprising an. effective amount of a compound of formula I or IV, in association with a carrier.

Figure 2:
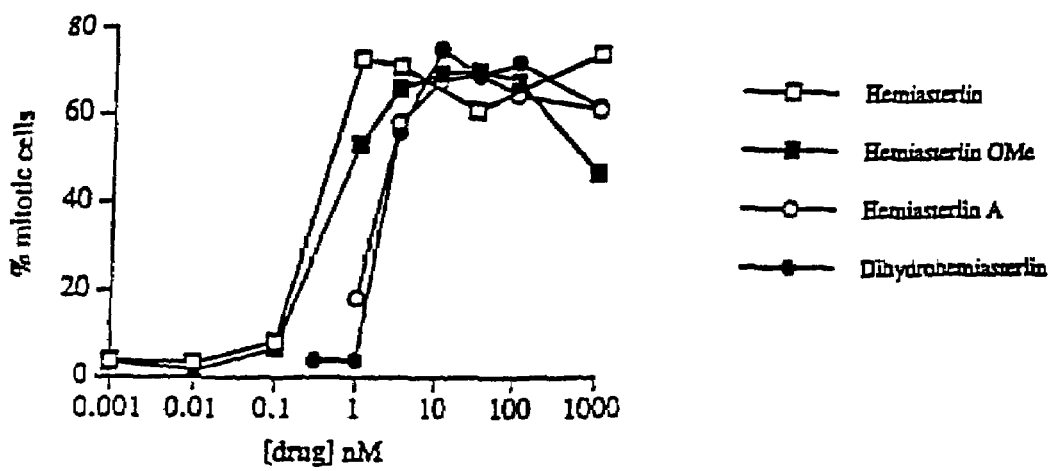
FIG. 2 shows the antimitotic activity of chemically modified Hemiasterlins.

The invention will now be further described, by way of example with reference to FIGS. 1 and 2 which are graphs relating to antimitotic activity.

Procedure 1:—Isolation of Naturally Occurring Compounds

Specimens of *Cymbastela* sp. were collected by hand using SCUBA on reefs off Mandang, Papua, New Guinea. Freshly collected sponge was frozen on site and transported to Vancouver, Canada, over dry ice. The sponges were identified by a leading sponge taxonomy expert Professor R. van Soest. A voucher sample was been deposited at the Institut voor Systematrek en Populatiebiologie-Zoologisch Museum, University of Amsterdam.

The thawed sponge (260 g dry wt) was extracted exhaustively with a solution of $CH_2Cl_2$/MeOH (1:1). Evaporation of the organic extract in vacuo gave an aqueous suspension. MeOH was added to give a 9:1 MeOH:$H_2O$ solution (1 l), which was extracted with hexanes (4×250 ml). The hexane extracts were combined and concentrated in vacuo to yield an orange oil. Water was added to the MeOH solution to give a 1:1 MeOH/$H_2O$ solution, which was extracted with $CHCl_3$ (4×250 ml). The combined $CHCl_3$ layers were concentrated in vacuo to yield an orange oil (3.5 g). Repeated size exclusion chromatography on Sephadex LH-20 eluting with MeOH yielded a number of crude geodiamolides and hemiasterlins. Pure geodiamolide G (Compound 1 below) (2 mg, 0.0007% dry wt) was obtained via reversed-phase HPLC (MeOH/$H_2O$ 60:40). Reversed-phase isocratic HPLC (0.05% TFA:MeOH 1:1) afforded hemiasterlin A (Compound 2 below –32 mg, 0.012% dry wt) and hemiasterlin B (Compound 3 below –1 mg, 0.0004% dry wt). These compounds are novel. The reversed-phase isocratic HPLC using TFA and MeOH also yielded the known compound hemiasterlin (Compound A below –40 mg, 0.015% dry wt). This was used to prepare a novel acylated and esterified compound described later.

Geodiamolide G (compound 1): colourless glass; IR (neat) 3313, 2977, 2933, 1732, 1675, 1635, 1505, 1455, 1417, 1377, 1285, 1217, 1102, 1083, 1052, 952, 827, 754 $cm^{-1}$; NMR data, Table 1 below; HREIMS, $M^+$ m/z 655.1760 ($C_{28}H_{38}N_3O_7I$ ΔM 0.6 mmu).

Hemiasterlin A (Compound 2): white solid $[\alpha]D=-45°$ (c 0.25, MeOH); UV (MeOH) λmax (ε) 218 (23,400), 280 nm (2,800); IR (neat) 3418, 2966, 1689, 1680, 1643 $cm^{-1}$; NMR data, Table 2 below; HRFABMS, $MH^+$ m/z 513.3471 ($C_{29}H_{45}O_4N_4$ ΔM 3.0 mmu).

Hemiasterlin B (Compound 3): white solid; CD(MeOH) $(\Theta)_{226}$ 10,800; NMR data, Table 2 below; HRFABMS, $MH^+$ m/z 499.3319 ($C_{28}H_{43}O_4N_4$ ΔM 3.4 mmu).

Hemiasterlin (Compound A): white solid; $[\alpha]D=-77°$ (c 0.07, MeOH); UV (MeOH) λmax (ε) 216 (15,400), 273 nm (1,600); IR (neat) 3412, 2962, 1650, 1635 $cm^{-1}$; NMR data, Table 2 below; HRFABMS, $MH^+$ m/z 527.3594 ($C_{30}H_{47}O_4N_4$ ΔM –0.35 mmu).

Product identification, including assignment of stereochemical configurations, was achieved by a range of techniques, including NMR, mass spectroscopy and optical rotation measurements, with cross-reference to analyses reported in the literature, for compounds already known. In the case of compounds 2 and 3 CD and chemical degradation analyses were carried out to assist the stereochemical determination.

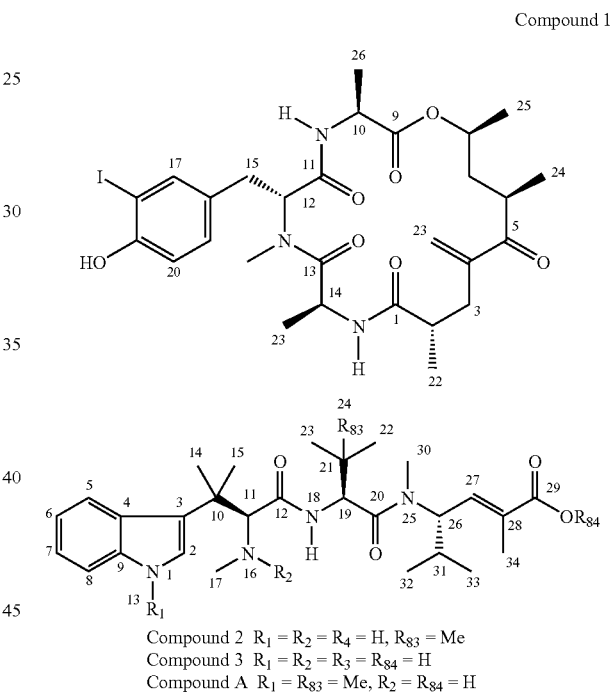

Compound 1

Compound 2 $R_1 = R_2 = R_4 = H$, $R_{83} = Me$
Compound 3 $R_1 = R_2 = R_3 = R_{84} = H$
Compound A $R_1 = R_{83} = Me$, $R_2 = R_{84} = H$

TABLE 1

NMR Data for Geodiamolide G (Compound 1). Recorded in $CDCl_3$ at 500 MHz.

| Carbon | δ $^{13}C^a$ | δ $^1H$ | COSY | $HMBC^b$ |
|---|---|---|---|---|
| 1 | 174.5 | | | H3.H3'.H14.H22.NH(14) |
| 2 | 41.0 | 2.46.m | H3.H3'.H22 | H3'.H22 |
| 3 | 37.7 | 2.55.ddJ=12.3.3.7Hz | H2.H3' | H22.H23.H23' |
| 3' | | 2.14.tJ=11.9Hz | H2.H3 | |
| 4 | 143.6 | | | H3.H23' |
| 5 | 205.1 | | | H3'.H23.H23'.H24 |
| 6 | 36.2 | 2.95 | H7'.H24 | H24 |
| 7 | 38.8 | 1.82.dddJ=14.6.9.5.2.8Hz | H7'.H8 | H24.H25 |
| 7' | | 1.61.dddJ=14.6.10.9.2.8Hz | H6.H7 | |
| 8 | 69.7 | 5.11.m | H7.H25 | H25 |
| 9 | 170.6 | | | H10.H26 |
| 10 | 49.1 | 4.51.daJ=7.3.7.2Hz | H26.NH(10) | H26 |

TABLE 1-continued

NMR Data for Geodiamolide G (Compound 1). Recorded in CDCl$_3$ at 500 MHz.

| Carbon | δ $^{13}$C[a] | δ $^1$H | COSY | HMBC[b] |
|---|---|---|---|---|
| NH(10) | | 6.35.dJ=7.3Hz | H10 | |
| 11 | 168.9 | | | H12.H15' |
| 12 | 57.1 | 5.06.ddJ=7.9.8.9Hz | H15.H15 | H15.H15'.H27 |
| 13 | 174.4 | | | H12.H14.H27.H28.NH(14) |
| 14 | 45.1 | 4.72.daJ=7.0.6.9Hz | H28.NH(14) | H28 |
| NH(14) | | 6.19.dJ=7.0Hz | H14 | |
| 15 | 33.2 | 3.12.ddJ=14.6.7.9Hz | H12.H15' | H12.H17.H21 |
| 15' | | 2.90.ddJ14.6.8.9Hz | H12.H15 | |
| 16 | 130.3 | | | H15.H15'.H20 |
| 17 | 138.2 | 7.45.dJ=1.4Hz | H21 | H15.H15'.H21 |
| 18 | 85.2 | | | H17.H20 |
| 19 | 154.5 | | | H17.H21 |
| 20 | 115.6 | 6.88.dJ=8.2Hz | H21 | |
| 21 | 130.6 | 7.04.ddJ=8.2.1.4Hz | H17.H20 | H17 |
| 22 | 17.9 | 1.15.dJ=6.4Hz | H2 | |
| 23 | 127.8 | 5.90.s | | H3' |
| 23' | | 5.78.s | | |
| 24 | 17.8 | 1.09.dJ=7.1Hz | H6 | |
| 25 | 20.8 | 1.28.dJ=6.3Hz | H8 | |
| 26 | 18.3 | 1.32.dJ=7.2Hz | H10 | H10 |
| 27 | 30.7 | 2.97.s | | H12 |
| 28 | 19.2 | 1.04.dJ=6.9Hz | H14 | |

[a]Obtained from HMQC and HMBC spectra only.
[b]Proton resonances that are correlated to the carbon resonance in the δ $^{13}$C column.

TABLE 2

NMR Data for the hemiasterlins, Compounds 2, 3 and A. Recorded in DMSO-d$_6$ at 500 MHz.

| | Hemiasterlin | | Hemiasterlin A | | | Hemiasterlin B | | |
|---|---|---|---|---|---|---|---|---|
| Carbon | δ $^{13}$C | δ $^1$H | δ $^{13}$C | δ $^1$H | HMBC[a] | δ $^{13}$C[b] | δ $^1$H | HMBC[a] |
| 1-N | | | | 10.93.s | | | 10.88.s | |
| 2 | 128.7 | 7.16.s | 122.9 | 7.11.s | H1 | 122.9 | 7.06.s | |
| 3 | 116.5 | | 120.4 | | H2.5.6.14.15 | 119.0 | | H14.15 |
| 4 | 125.0 | | 124.8 | | H1.2.8 | 124.8 | | H2.8 |
| 5 | 120.6 | 8.09.d.J=8Hz | 120.2 | 7.80.d.J=8Hz | | 120.0 | 7.98.d.J=7.8Hz | |
| 6 | 121.1 | 7.07.t.J=8Hz | 120.7 | 7.06.t.J=8Hz | | 120.4 | 7.05.t.J=7.8Hz | |
| 7 | 118.4 | 7.20.t.J=8Hz | 118.1 | 6.96.t.J=8Hz | H8 | 117.8 | 6.95.t.J=7.8Hz | H8 |
| 8 | 110.0 | 7.44.d.J=8Hz | 111.8 | 7.35.d.J=8Hz | | 111.4 | 7.38.d.J=7.8Hz | H7 |
| 9 | 137.7 | | 137.3 | | H1.2.5.6 | 137.2 | | H2 |
| 10 | 37.5 | | 37.9 | | H11.14.15 | 37.5 | | H14.15 |
| 11 | 67.5 | 4.44.d.J=6Hz | 71.7 | 3.47.s | H14.15.17 | 69.3 | 3.47.bs | |
| 12 | 166.0 | | 171.2 | | H11 | | | |
| 13 | 32.4 | 3.75.s | | | | | | |
| 14 | 27.0 | 1.41.s | 27.5 | 1.41.s | H15 | 27.3 | 1.38.s | H15 |
| 15 | 22.5 | 1.38.s | 23.2 | 1.37.s | H11.14 | 22.5 | 1.34.s | H14 |
| 16-N | | 7.38.bs | | | | | | |
| 17 | 33.4 | 2.24.s | 35.2 | 1.92.s | H11 | 35.0 | 1.93.s | |
| 18-N | | 8.87.s | | 7.84.bd.J=9Hz | | | | |
| 19 | 56.2 | 4.84.d.J=8Hz | 53.8 | 4.79.d.J=9Hz | | 53.8 | 4.58.t.J=8Hz | H22.23 |
| 20 | 170.1 | | 170.9 | | H19.30 | 171.0 | | H30 |
| 21 | 34.6 | | 34.7 | | H19.22.23.24 | 30.0 | 2.11.m | H19.22 |
| 22 | 26.3 | 0.99.s | 26.2 | 0.93.s | H19.23.24 | | 0.84.d.J=6.3Hz | |
| 23 | 26.3 | 0.99.s | 26.2 | 0.93.s | H19.22.24 | | 0.89.d.J=6.3Hz | |
| 24 | 26.3 | 0.99.s | 26.2 | 0.93.s | H19.22.23 | | | |
| 26 | 55.6 | 4.93.t.J=10Hz | 55.9 | 4.91.t.J=9Hz | H30.32.33 | 55.8 | 4.87.t.J=10Hz | H30.32.33 |
| 27 | 138.3 | 6.66.d.J=10Hz | 138.2 | 6.63.d.J=9Hz | H26.34 | 137.7 | 6.63.d.J=8.8Hz | H26.34 |
| 28 | 131.6 | | 131.8 | | H26.34 | 131.5 | | H34 |
| 29 | 168.5 | | 168.6 | | H27.34 | 168.5 | | H34 |
| 30 | 31.1 | 3.03.s | 30.9 | 2.97.s | H26 | 30.0 | 2.98.s | |
| 31 | 28.7 | 2.01.m | 28.8 | 1.96.m | H26.32.33 | 28.7 | 2.08.m | H32.26 |
| 32 | 19.3 | 0.80.d.J=7Hz | 19.3 | 0.77.d.J=6.5Hz | H33 | | 0.74.d.J=6.1Hz | |
| 33 | 18.9 | 0.78.d.J=7Hz | 18.7 | 0.70.d.J=6.5Hz | H32 | | 0.80.d.J=6.1Hz | |
| 34 | 13.5 | 1.80.s | 13.5 | 1.77.s | H27 | 13.0 | 1.75.s | H27 |

[a]Proton resonances that are correlated to the carbon resonance in the δ $^{13}$C column.
[b]Obtained from HMQC and HMBC correlations.

In another example, specimens of *Cymbasyela* sp. were collected by hand using SCUBA on the reefs of Madang, Papua, New Guinea. Fresh sponge was frozen on site and transported to Vancouver, Canada, over dry ice. The freeze-dried sponge (157 g dry wt.) was extracted sequentially with hexane, carbon tetrachloride, chloroform and methanol (3×8 liters). The extracts were concentrated in vacuo to yield 6 g, 0.76 g, 1.24 g and 1.1 g respectively for each solvent. Repeated size exclusion chromatography of the chloroform extract, on Sephadex LH-20 with methanol, yielded a mixture of crude hemiasterlins and criamides. Reversed phase HPLC, 50:50 0.05% TFA:MeOH afforded pure Hemiasterlin (60 mg, 0.038% dry wt.) (Compound A above); Hemiasterlin-A (55 mg, 0.035% dry wt.) (Compound 2 above); Hemiasterlin-B (3 mg, 0.0019% dry weight) (Compound 3 above); Criamide-A (2 mg, 0.0013% dry wt.) (Compound 6 below); Criamide-B (2 mg, 0.0013% dry wt.) (Compound 7 below).

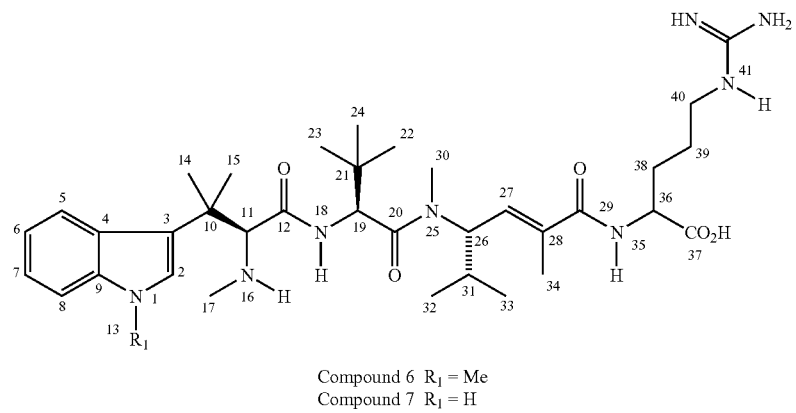

Compound 6 R₁ = Me
Compound 7 R₁ = H

Product identification of compounds 6 and 7, including assignment of stereochemical configurations, was achieved by a range of techniques as described above for the other examples. NMR data is provided in Table 3 below.

TABLE 3

NMR Data for Criamide B (Compound 7) and Criamide A (Compound 6)

| | Criamide B | | | | Criamide A | |
|---|---|---|---|---|---|---|
| Carbon no. | δ $^{13}$C (ppm) (125 MHz) | δ $^{1}$H (ppm) (500 MHz) | COSY (500 MHz) | HMBC (500 MHz) | δ $^{1}$H (ppm) (500 MHz) | COSY (500 MHz) |
| 1-N | | 11.14.s | | | | |
| 2 | 124.2 | 7.16.d.J=2.3 | | | 7.17.s | |
| 3 | 117.1 | | | H1.2.14.15 | | |
| 4 | 137.7 | | | H5.7 | | |
| 5 | 120.2 | 8.08.d.J=7.3 | H6 | H7 | 8.10.d.J=7.9 | H6 |
| 6 | 118.0 | 7.03.t.J=7.3 | H5.7 | H8 | 7.08.t.J=7.0 | H5.7 |
| 7 | 120.9 | 7.12.t.J=7.3 | H6.8 | H5 | 7.21.t.J=8.2 | H6.8 |
| 8 | 112.0 | 7.41.d.J=8.0 | H7 | H6 | 7.46.d.J=8.5 | H7 |
| 9 | 124.7 | | | H1.2.6 | | |
| 10 | 37.6 | | | H14.15 | | |
| 11 | 67.6 | 4.45.d.J=9.0 | H16-A | H14.15 | 4.44.d.J=9.2 | H16-A |
| 12 | 165.8 | | | H19 | | |
| 13 | | | | | 3.75.s | |
| 14 | 27.2 | 1.42.s | | H15 | 1.42.s | |
| 15 | 22.0 | 1.38.s | | H14 | 1.38.s | |
| 16 | | A 7.30.bs | H16-B.11.17 | | 7.35.bs | H16-B.11.17 |
| | | B 8.77.bs | H16-A.17 | | 8.84.bs | H16-A.17 |
| 17 | 33.5 | 2.23.t.J=4.8 | H16A.16B | | 2.24.bs | H16A.16B |
| 18-N | | 8.86.d.J=9.2 | H19 | | 8.87.d.J=6.1 | H19 |
| 19 | 55.5 | 4.88.d.J=8.2 | H18 | H22.23.24 | 4.88.d.J=8.5 | H18.H21 |
| 20 | 170.1 | | | H19.26.30 | | |
| 21 | 34.9 | | | H22.23.24 | | |
| 22 | 26.3 | 1.0.s | | H19.23.24 | 1.00.s | |
| 23 | 26.3 | 1.0.s | | H19.22.24 | 1.00.s | |
| 24 | 26.3 | 1.0.s | | H19.22.23 | 1.00.s | |
| 26 | 55.9 | 4.98.t.J=9.8 | H27.31 | H30.32.33 | 4.98.t.J=9.8 | H27.31 |
| 27 | 132.4 | 6.30.d.J=9.0 | H26 | H26.34 | 6.30.d.J=8.5 | H26 |
| 28 | 135.4 | | | H26.34 | | |
| 29 | 168.7 | | | H27.29.34 | | |

TABLE 3-continued

NMR Data for Criamide B (Compound 7) and Criamide A (Compound 6)

| | Criamide B | | | | Criamide A | |
|---|---|---|---|---|---|---|
| Carbon no. | δ $^{13}$C (ppm) (125 MHz) | δ $^{1}$H (ppm) (500 MHz) | COSY (500 MHz) | HMBC (500 MHz) | δ $^{1}$H (ppm) (500 MHz) | COSY (500 MHz) |
| 30 | 30.9 | 3.04.s | | H26 | 3.01.s | |
| 31 | 28.7 | 2.01.m | H26.32.33 | H32.33 | 1.94.m | H26.32.33 |
| 32 | 19.5 | 0.83.d.J=6.5 | H31 | H33 | 0.83.d.J=7.7 | H31 |
| 33 | 19.2 | 0.78.d.J=6.5 | H31 | H32 | 0.77.d.J=7.7 | H31 |
| 34 | 14.2 | 1.82.s | | H27 | 1.82.s | |
| 35-N | | 8.02.d.J=7.6 | H36 | | 8.03.d.J=7.6 | H36 |
| 36 | 51.8 | 4.27.m | H35.38-A.38-B | | 4.26.dd.J=4.0.9.0 | H35.38-A.38-B |
| 38 | 27.7 | A 1.81.m | H36.38-B | | A 1.79.m | H36.38-B |
| | | B 1.67.m | H38-A.39 | | B 1.69.m | H38-A.39 |
| 39 | 24.6 | 1.51.m | H38-B.40 | | 1.49.m | H38-B.40 |
| 40 | 40.0 | 3.10.dd.J=5.9.7.1 | H39.41 | | 3.09.dd.J=6.0.7.0 | H39.41 |
| 41-N | | 7.53.t.J=5.9 | H40 | | 7.59.t.J=5.0 | H40 |

Procedure 2: Derivatisation of Naturally Occurring Compounds

The following compounds 4 and 5, were respectively prepared from compounds A and 2 above.

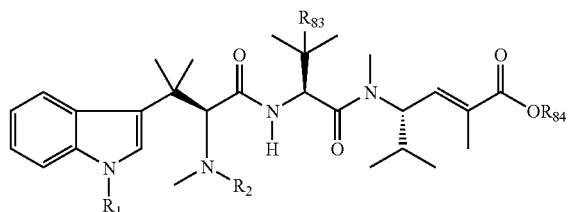

Compound 4 $R_1 = R_{83} = R_{84} = Me$, $R_2 = COCH_3$
Compound 5 $R_1 = H$, $R_2 = COCH_3$, $R_{83} = R_{84} = Me$ They were prepared by firstly converting compounds A and 2 to their methyl esters, then by acylating the esters.

To prepare the methyl esters of compounds A and 2, diazomethane was prepared in the standard fashion from 1-methyl-3-nitro-1-nitrosoguanidine (MNNG) using an Aldrich MNNG-diazomethane kit. The resulting yellow diazomethane solution (3 ml ether) was added to 1 mg of peptide A or 2, dissolved in 3 ml of chloroform. The reaction mixture was left at ambient temperature for one hour then the solvents were removed in vacuo.

To then acylate the esterified peptides, approximately 1 mg of each esterified peptide was stirred overnight under an argon atmosphere with freshly distilled (from NaOH) pyridine and acetic anhydride (1.0 ml each). Excess reagents were removed in vacuo to yield the pure N-acetyl peptide esters, compounds 4 and 5, which are characterised as follows.

Hemiasterlin, N-acetyl methyl ester (Compound 4): white solid; CD(MeOH) (Θ)$_{231}$+13,300; $^{1}$H NMR CD$_2$CL$_2$, 500 MHz) δ 0.44 (s), 0.84 (d, J=6.6 Hz), 0.87 (d, J=6.6 Hz), 1.39 (s), 1.59 (s), 1.86 (s), 2.04 (m), 2.16 (s), 2.93 (s), 3.15 (s), 3.70 (s), 3.76 (s), 4.41 (d, J=9 Hz), 5.03 (t, J=9 Hz), 6.18 (d, J=8 Hz), 6.39 (s), 6.64 (d, J=8 Hz), 7.10 (s), 7.15 (t, J=8 Hz), 7.24 (t, J=8 Hz), 7.32 (d, J=8 Hz), 8.29 (d, J=9 Hz); EIHRMS, M$^+$ m/z 582.3796 (C$_{33}$H$_{50}$N$_4$O$_5$ ΔM 1.5 mmu).

Hemiasterlin A, N-acetyl methyl ester (Compound 5): white solid; CD(MeOH) (Θ)$_{231}$+10,400; $^{1}$H NMR CD$_2$CL$_2$, 500 MHz) δ 0.48 (s), 0.83 (d, J=6.6 Hz), 0.88 (d, J=6.6 Hz), 1.40 (s) 1.54.(s), 1.85 (s), 1.98 (m), 2.16 (s), 2.93 (s), 3.15 (s), 3.70 (s), 4.48 (d, J=10.1 Hz), 5.02 (t, J=10 Hz), 6.19 (d, J=9 Hz), 6.37 (s), 6.65 (d, J=10.5 Hz), 7.17 (t, J=7 Hz), 7.20 (t, J=7 Hz), 7.23 (s), 7.40 (d, J=7 Hz), 8.30 (d, J=10 Hz), 8.31 (s); EIHRMS, M$^+$ m/z 568.3626 (C$_{32}$H$_{48}$N$_4$O$_5$ ΔM 0.1 mmu).

Procedure 3: Totally Synthetic Method

The process for preparing compounds described herein by a totally synthetic method involves, in general terms, the coupling of amino acids. Thus, the preparation of the compound

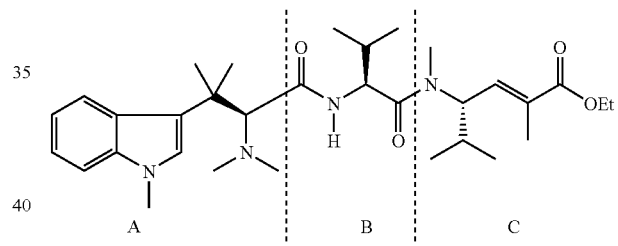

involves coupling amino acids corresponding to units A, B and C. Criamide compounds which include an additional moiety D coupled to end C of the compound shown above can be prepared by coupling an amino acid corresponding to the desired moiety D to the peptide A-B-C.

The preparations of amino acids A and C are described below. Amino acid B is commercially available.

1. Preparation of Amino Acid C (N-methylhomo Vinylogous Valine Ethyl Ester)

Scheme 1 below provides a summary of the procedures described hereinafter.

(a) Preparation of N-Boc,N-Me-L-valine (1)

N-Boc-L-valine (5 g; 23 mmol) and methyl iodide (1.59 ml; 25.3 mmol) were dissolved in THF (65 ml) and the solution was cooled to 0° C. under argon. Sodium hydride dispersion (2.03 g; 50.6 mmol) was added cautiously with gentle stirring. The suspension was stirred at room temperature for 16 h. Ethyl acetate (30 ml) was then added (to consume the sodium hydroxide formed from the excess sodium hydride), followed by water, drop wise, to destroy the excess sodium hydride. The solution was evaporated to dryness, and the oily residue partitioned between ether (25 ml) and water (50 ml). The ether layer was washed with 5% aqueous NaHCO$_3$ (25 ml), and the combined aqueous extracts acidified to pH 3 with aqueous citric acid. The product was extracted into ethyl acetate (3×25 ml), the extract washed with water (2×25 ml), 5% aqueous sodium thiosulfate (2×25 ml; to remove iodine), and water (2×25 ml), dried over MgSO$_4$ and evaporated to give a yellow oil. The procedure was repeated to improve the overall yield. Final yield was 3.53 g; 70.6%. $^1$H nmr (CDCl$_3$; 400 MHz) δ 0.86 (d, 3H, J=7 Hz), 0.97 (d, 3H, J=7 Hz),1.41 (s, 9H),2.17 (bs, 1H),2.80 & 2.82 (2 s, 3H), 4.05 (d, 0.5H, J=10 Hz), 4.26 (d, 0.5H, J=10 Hz), 10.8 (bs, 1H).

(b) Preparation of N-Boc,N-Me-L-valine-N-Me,N-Ome (Weinreb amide)(2)

N-Boc,N-Me-L-valine (3.2 g; 13.9 mmol), N,O-dimethylhydoxylamine hydrochloride (1.5 g; 15 mmol) and triethyl amine (2.1 ml; 30 mmol) were dissolved in CH$_2$Cl$_2$ (30 ml) and the solution cooled to −10° C. under argon. Dicyclohexylcarbimide (3.1 g; 15 mmol) was dissolved in 15 ml of CH$_2$Cl$_2$ and added drop wise to the reaction mixture over 10 minutes. The solution was stirred for an additional 15 minutes at −10° C. and then for 1 h at room temperature at which time it was filtered and the excess solvents removed in vacuo. The oil was dissolved in EtOAc (50 ml) and washed with 5% HCl (2×25 ml), water (2×25 ml), 5% NaHCO$_3$ (2×25 ml), and water (2×25 ml), dried over MgSO$_4$ and evaporated to yield a yellow oil (3.4 g; 85% yield).

$^1$H nmr (CDCl3; 400 MHz) δ (0.82 (t, 6H J=7 Hz), 1.38 (s, ~3 H), 1.41 (s, ~6H), 2.16 (m, 1H), 2.73 (s, ~1H), 2.76 (s, ~2H), 3.13 (s, 3H), 3.62 (s, ~1H), 3.65 (s, ~2H). Doubling of peaks caused by rotamers around the N-Boc group.

(c) Preparation of N-Boc, N-Me-L-valine Aldehyde (3)

Weinreb amide (226 mg; 0.78 mmol) was dissolved in THF (8 ml) and cooled to −78° C, then added drop wise to a dispersion of LiAlH$_4$ (35 mg; 0.86 mmol) in THF at −78° C. The reaction was stirred for 0.5 h at which time it was quenched with Na$_2$SO$_4$.10H$_2$O (251 mg; 0.78 mmol) and allowed to warm to room temperature. The solution was filtered through celite and the excess solvents removed in vacuo to yield a colourless oil. Normal phase silica gel chromatography, eluting with 1:6 ethyl acetate: hexanes, afforded pure N-Boc,N-Me-L-valine aldehyde as a clear oil (116 mg; 68%).

$^1$H nmr (CDCl$_3$; 400 MHz) δ 0.84 (d, 3H, J=7 Hz), 1.03 (d, 3H, J=7 Hz), 1.40 (s,9H), 2.20 (bs, 1H), 2.72 (s,2H), 2.84 (s,1H) 3.55 (d, 0.5 H, J=10 Hz), 4.02 (d,0.5H, J=10 Hz), 9.58 (bs, 1H).

(d) Preparation of N-Boc-MHVV-OEt (4)

N-Boc,N-Me-valine aldehyde (120 mg; 0.56 mmol) was dissolved in a 1:1 mixture of THF:H$_2$O (6 ml) and the (carbethoxy ethylidene)triphenylphosphane (222 mg; 6.2 mmol) was added and the reaction stirred at room temperature for 4 h. Normal phase silica gel chromatography, eluting with 1:6 ethyl acetate: hexanes, afforded the N-Boc-homo vinylogous valine ethyl ester as a clear oil (212 mg; 71%).

$^1$H nmr (CDCl3; 400MHz) δ 0.82 (d, 3H, J=7 Hz), 0.87 (d, 3H, J=7 Hz), 1.27 (t,3H, J=7 Hz), 1.42 (s, 9H), 1.85 (m, 1H), 1.87 (s, 3H), 2.69 (bs, 3H) 4.17 (q, 2H, 7 Hz), 4.28 (bs, 0.5H), 4.53 (bs, 0.5H), 6.62 (d, 1H, J=9 Hz).

(e) Preparation of MHVV-OEt (5)

N-Boc-MHVV-OEt (200 mg; 67 mmol) was dissolved in 1 ml of 1:1 CH$_2$Cl$_2$: trifluoroacetic acid mixture and stirred under argon for 0.5 h. Excess solvents were removed in vacuo and the oily residue was twice redissolved in CH$_2$Cl$_2$ (25 ml) and concentrated to remove any traces of TFA. The final product was a white amorphous solid (207 mg, 99%).

$^1$H nmr (CDCl3; 400 MHz) δ 0.82 (t, 6H, J=7 Hz), 1.27 (t, 3H, J=7 Hz), 1.42 (s, 9H), 1.85 (m, 1H), 1.87 (s, 3H), 2.69 (bs, 3H), 3.9 (m, 1H), 4.17 (q, 2H, 7 Hz), 6.62 (d, 1H, J=9 Hz) 8.1 (bs, 0.5H), 8.3 (bs, 0.5H), 12.9 (bs, 1H).

2. Preparation of Amino-acid A (N-Boc-tetramethyltryptophan Derivative)

Scheme 2 below provides a summary of the procedures described hereinafter for the preparation of amino acid A and derivatives which are described herein:

(a) Preparation of Methyl Ester (7)

To a stirred suspension of indol-3-acetic acid (6) (1.07 g, 6.11 mmol) in ether (20 ml) at room temperature was added an ethereal solution of diazomethane drop wise until the yellow colour of the diazomethane persisted in the reaction mixture, and tlc analysis showed complete consumption of starting material. Excess diazomethane was removed under a stream of argon and the remaining solvent removed in vacuo. The crude oil thus obtained was purified by flash column chromatography (50% ether in pet. ether), to afford methyl ester, (7) as an off-white solid (1.16 g, 100%).

Mp: 47-48° C. IR (CHCl$_3$ soln): 3409 (s, NH), 1729 (s, C=0), 1621 (w, C=C). $^1$H NMR (400 MHz, CDCl$_3$) δ: 3.71 (3H,s, OCH$_3$), 3.79 (2H,s, CH$_2$CO$_2$CH$_3$), 7.03 (1H, s, =CHNH), 7.15 (1H,t,J=7.8 Hz,ArH), 7.20 (1H,t,J=7.8 Hz,ArH), 7.31 (1H,d,J=7.8 Hz, ArH), 7.63 (1H,d,J=7.8 Hz, ArH), 8.12 (1H,br,s,NH). $^{13}$C NMR (75.3 MHz, CDCl3) δ: 172.6, 136.0, 127.1, 123.1 122.1, 119.6, 118.7, 111.2, 108.1, 51.9, 31.9. LRMS (EI): 189 (M$^+$, 25%), 130 (100%). HRMS (EI) Calcd. for C$_{11}$H$_{11}$O$_2$N: 189.07898; found: 189.07866. Anal. Calcd. for: C$_{11}$H$_{11}$O$_2$N: C, 69.83; H, 5.86; N, 7.40. Found: C, 69.47; H, 5.91; N, 7.50

(b) Preparation of Di Methyl Ester (8)

To a stirred, cooled (−78° C.) suspension of potassium bis(trimethylsilyl) amide (4.90 g 24.6 mmol) in dry THF (100 ml) under argon was added a solution of methyl ester (7) (1.57 g, 8.31 mmol) in THF (30 ml+20 ml washings) via cannula. The reaction mixture was warmed to 0° C. and stirred for two hours before recoiling to −78° C. Freshly distilled methyl iodide (5.2 ml, 82.8 mmol) was added, the mixture allowed to warm to 0° C. and stirring continued for three hours or until tlc analysis showed complete reaction. The reaction was quenched with water (100 ml) and then extracted with ether (3×100 ml), the combined organic extracts were washed with brine (100 ml), dried with magnesium sulfate and concentrated in vacuo. The resulting crude oil was purified by flash column chromatography (25% ether in pet.ether) to afford methyl ester (8) as a viscous pale yellow oil (1.61 g, 89%).

IR (neat): 1734(s, C=O), 1615, 1550 (w, C=C). $^1$H NMR (400 MHz, CDCl$_3$) δ: 1.61 (3H, d,J=7.1 Hz, CH(CH$_3$)), 3.67 (3H, s, NCH$_3$), 3.75 (3H,s, OCH$_3$), 4.01 (1H,q,J=7.1 Hz, CH(CH$_3$)CO$_2$CH$_3$), 7.00 (1H, s =CHNCH$_3$), 7.13 (1H,t,J=7.8 Hz,ArH), 7.24 (1H,t,J=7.8 Hz, ArH), 7.30 (1H,d,J=7.8 Hz, Ar H), 7.68 (1H,d,J=7.8 Hz, ArH). $^{13}$C NMR (75.3 MHz, CDCl$_3$) δ: 175.6, 136.9, 126.7, 126.2, 121.7, 119.2, 119.0, 113.9, 109.2, 51.9, 36.7, 32.7, 18.0. LRMS (EI): 217 (M$^+$, 18%), 158 (100%). HRMS (EI) Calcd. for C$_{13}$H$_{15}$O$_2$N: 217.11028; found: 217.11013. Anal. Calcd. for: C$_{13}$H$_{15}$O$_2$N: C, 71.87; H, 6.96; N, 6.45. Found: C, 71.52; H,6.80; N, 6.26.

(c) Preparation of Tri Methyl Ester (9)

To a stirred, cooled (−78° C.) suspension of potassium bis(trimethylsilyl)amide (2.90 g, 14.5 mmol) in dry THF (60 ml) under argon was added a solution of methyl ester (8) (1.25 g, 5.76 mmol) in THF (30 ml+20 ml washings) via cannula. The reaction mixture was warmed to 0° C. and stirred for two hours before re-coiling to −78° C. Freshly distilled methyl iodide (3.5 ml, 57.6 mmol), was added, the mixture allowed to warm to 0° C. and stirring continued for three hours or until tlc analysis showed complete reaction. The reaction was quenched with water (60 ml) and then extracted with ether (3×75 ml), the combined organic extracts were washed with brine (75 ml), dried with magnesium sulfate and concentrated in vacuo. The resulting crude oil was purified by flash column chromatography (20% ether in pet.ether) to afford the methyl ester (9) as an off-white solid (1.22 g 92%).

Mp: 99-101° C. IR (CHCl$_3$ soln): 1727 (s, C=O), 1618, 1550 (w, C=C). $^1$H NMR (400 MHz, CDCl$_3$) δ: 1.70 (6H,S, CCH$_3$(CH$_3$)), 3.64 (3H,s,NCH$_3$), 3.75 (3H,s,OCH$_3$), 6.94 (1H,s =CHNH), 7.10 (1H,t,J=7.9 Hz ArH), 7.22 (1H,t,J=7.9 Hz, ArH), 7.29 (1H,d,J=7.8 Hz,ArH), 7.64 (1H,d,J=7.8 Hz, ArH). $^{13}$C NMR (75.3 MHz, CDCl$_3$) δ: 177.6, 137.4, 125.9, 125.2, 121.5, 120.2, 119.1, 119.0, 109.3, 52.1, 41.9, 32.7, 26.3. LRMS (EI): 231 (M$^+$, 15%), 172 (100%). HRMS (EI) Calcd. for C$_{14}$H$_{17}$O$_2$N: 231.12593; found: 231.12572. Anal. Calcd for: C$_{14}$H$_{17}$O$_2$N: C, 72.70; H, 7.41; N, 6.06. Found: C, 72.83; H, 7.44; N, 6.04.

(d) Preparation of Alcohol (10)

To a stirred colled (−78° C.) solution of methyl ester (9) (1.38 g, 5.97 mmol) in dry ether (70 ml) under an argon atmosphere was added DIBAL (14.9 ml, 1.0M in hexanes, 14.9 mmol). The resulting solution was allowed to warm to 0° C. and stirring was continued for three hours. The reaction was quenched by addition of water (30 ml), allowed to warm to room temperature whereupon Rochelles salt (30 ml) was added. The organic layer was separated and the aqueous layer was extracted with ether (2×50 ml). The combined organic extracts were washed with brine (50 ml), dried with magnesium sulfate and concentrated in vacuo. The crude mixture was purified by flash column chromatography (50% ether in pet.ether) to afford the alcohol (10) as a white solid (1.14 g, 94%).

Mp: 80-82° C. IR (CHCl$_3$ soln): 3400 (br, s, OH), 1614, 1545 (w, C=C). $^1$H NMR (400 MHz, CDCl$_3$) δ: 1.48 (6H,s, CCH$_3$(CH$_3$)), 3.75 (3H,s,NCH$_3$), 3.79 (2H,s,CH$_2$OH), 6.90 (1H,s =CHNH), 7.11 (1H,t,J=7.9 Hz ArH), 7.22 (1H,t,J=7.9 Hz, ArH), 7.32 (1H,d,J=7.8 Hz,ArH), 7.78 (1H,d,J=7.8 Hz, ArH). $^{13}$C NMR (75.3 MHz, CDCl$_3$) δ: 137.9, 127.1, 126.1, 121.5, 121.0, 119.4, 118.8, 109.6, 71.6, 37.7, 32.7, 25.5. LRMS (EI): 203 (M$^+$, 17%), 172 (100%). HRMS (EI) Calcd. for C$_{13}$H$_{17}$ON: 203.13101; found: 203.13052. Anal. Calcd for: C$_{13}$H$_{17}$ON: C, 76.81; H, 8.43; N, 6.89. Found: C, 76.89; H, 8.43; N, 6.70.

(e) Preparation of Aldehyde (11)

To a mixture of alcohol (10) (362 mg, 1.78 mmol) 4-methylmorpholine N-oxide (375 mg, 3.21 mmol) and 4A powdered molecular sieves (400 mg) in dry dichloromethane (12 ml) under an argon atmosphere at room temperature was added solid TPAP (35 mg, 0.0996 mmol) in one portion. The resulting black mixture was stirred at the same temperature for three hours, then filtered through celite to remove the molecular sieves and the filtrate concentrated in vacuo. The black oil was purified by flash column chromatography (20% ether in pet.ether) to afford the aldehyde (11) as an off-white solid (314 mg, 88%).

Mp: 61-63° C. IR (CHCl$_3$ soln): 1718 (s, C=O), 1610, 1542 (w, C=C). $^1$H NMR (400 MHz, CDCl$_3$) δ: 1.58 (6H,s, CCH$_3$(CH$_3$)), 3.70 (3H,s,NCH$_3$), 6.96 (1H,s, =CHNH), 7.10 (1H,dt,J=0.9, 8.0 Hz,ArH), 7.24 (1H,dt,J=0.9, 8.0 Hz Ar H), 7.32 (1H,dd,J=0.9, 8.0 Hz, ArH), 7.56 (1H,dd,J=0.9, 8.0 Hz,ArH), 9.49 (1H,s, CHO). $^{13}$C NMR (75.3 MHz, CDCl$_3$) δ: 202.2, 137.6, 126.6, 126.1, 121.8, 120.1, 119.3, 115.0, 109.5, 46.5, 32.8, 21.9. LRMS (EI): 201 (M$^+$, 13%), 172 (100%). HRMS (EI) Calcd. for C$_{13}$H$_{15}$ON: 201.1153; found: 201.11473. Anal. Calcd for: C$_{13}$H$_{15}$ON: C, 77.58; H, 7.51; N, 6.96. Found: C, 77.42; H, 7.58; N, 6.83.

(f) Preparation of Enol Ether (12)

To a stirred suspension of methoxymethyltriphenylphosphonium chloride (3.03 g, 8.84 mmol) in dry THF (40 ml) under an argon atmosphere at room temperature (water bath) was added potassium tert-butoxide (991 mg, 8.82 mmol) as a solid in one portion. The reaction mixture immediately turned a deep red colour, the water bath was removed and stirring continued for one and a half hours at room temperature. Aldehyde (11) (828 mg, 4.12 mmol) was added via cannula in THF (10 ml+5 ml washings), and stirring continued for a further two hours. The reaction mixture was diluted with water (30 ml) and extracted with ether (3×40 ml). The combined organic extracts were washed with brine (60 ml), dried with magnesium sulfate and concentrated in vacuo. The crude oil was purified by flash column chromatography (5% ether in pet.ether) to afford the required enol ether (12) as a 40:60 mixture of cis and trans isomers, (not separated) (873 mg, 92%). The purity of this mixture was checked by 200 MHz nmr and the mixture taken on and used in the following step without further characterisation.

$^1$H NMR (200 MHz, CDCl$_3$) δ: 1.52 (2.4H,s,CCH$_3$(CH$_3$)), 1.62 (3.6H,s,CCH$_3$CH$_3$)), 3.49 (1.8H,s, =OCH$_3$), 3.53 (1.2H,s, OCH$_3$), 3.73 (1.2H,s,NCH$_3$), 3.74 (1.6H,s,NCH$_3$) 4.60 (0.4H,d,J=6.9 Hz,=CHOMe), 5.13 (0.6H,d,J=12.7 Hz,=CHOMe), 5.78 (0.4H,d,J=6.9 Hz, CH=CHOMe), 6.32 (0.6H, d,J=12.7 Hz, CH=CHOMe), 6.83 (1H,s,=C HNH), 7.02-7.40 (3H,m,3×ArH), 7.73-7.78 (1H,m,ArH).

(g) Preparation of Aldehyde (13)

To a stirred solution of enol ether (12) (854 mg, 3.73 mmol) in dioxane (40 ml) and water (10 ml) at room temperature was added p-toluenesulfonic acid monohydrate (100 mg. 0.526 mmol), the resulting mixture was heated to 60° C. for sixteen hours. The reacton mixture was then diluted with water (40 ml) and extracted with ether (3×50 ml), the combined organic extracts were washed with brine (75 ml), dried with magnesium sulfate and concentrated in vacuo. The crude oil was purified by flash column chromatography (20% ether in pet.ether) to afford the desired aldehyde (13) as an off-white solid (696.2 mg, 86%).

Mp: 39-40° C. IR (CHCl$_3$ soln): 1718 (s, C=O), 1615, 1546 (w, C=C). $^1$H NMR (400 MHz, CDCl$_3$) δ: 1.55 (6H,s, CCH$_3$(CH$_3$)), 2.83 (2H,d,J=3.1 Hz, CH$_2$CHO), 3.74 (3H,s, =NCH$_3$), 6.82 (1H,s, =CHNH), 7.10 (1H,dt,J=1.0, 7.3 Hz ArH), 7.24 (1H,dt,J=1.0, 7.3 Hz, ArH), 7.32 (1H,dd, J=1.0, 7.3 Hz,ArH), 7.56 (1H,dd,J=1.0, 7.3 Hz ArH), 9.51 (1H,t,J=3.1 Hz CHO). $^{13}$C NMR (75.3 MHz, CDCl$_3$) δ: 204.1, 137.9, 125.6, 125.3, 121.4, 121.3, 120.7, 118.7, 109.6, 54.7, 33.6, 32.6, 29.2. LRMS (EI): 215 (M$^+$, 45%), 172 (100%). HRMS (EI) Calcd. for C$_{14}$H$_{17}$ON: 215.13101; found: 215.13103. Anal. Calcd for: C$_{14}$H$_{17}$ON: C, 78.10; H, 7.96; N, 6.51. Found: C, 78.22; H, 7.98; N, 6.41.

(h) Preparation of Acid (14)

To a solution of aldehyde (13) 234 mg, 1.09 mmol) in tert-butyl alcohol (6 ml) at room temperature was added 2-methyl-2-butene (8.0 ml, 2.0M in THF, 16.3 mmol). To the resulting solution was added a solution of sodium chlorite (148 mg, 1.63 mmol) and sodium hydrogen phoshpate (600 mg, 4.36 mmol) in water (6 ml). The resulting solution was stirred for twenty minutes at room temperature and then diluted with water (10 ml), acidified to pH 1-2 with dilute hydrochloric acid and extracted with ethyl acetate (3×25 ml). The combined organic extracts were concentrated in vacuo with trace amounts of water being removed by azeotropic distillation with toluene. The resulting crude mixture was purified by flash column chromatography (50% ether in pet.ether +1% acetic acid) to afford the acid (14) as an off white solid.

Mp: 139-140° C. IR (CHCl$_3$ soln): 3054, 2981 (s, br, OH), 1705 (s, C=O), 1620, 1540 (w, C=C).
$^1$H NMR (400 MHz, CDCl$_3$) δ: 1.63 (6H,s,CCH$_3$(CH$_3$)), 2.88 (2H,c, CH$_2$CO$_2$H), 3.74 (3H,s, =NCH$_3$), 6.87 (1H,s,=CHNH), 7.10 (1H,dt,J=8.0 Hz ArH), 7.24 (1H,t, J=8.0 Hz, ArH), 7.32 (1H,d,J=8.0 Hz,ArH), 7.56 (1H,d,J=8.0 Hz ArH). $^{13}$C NMR (75.3 MHz, CDCl$_3$) δ: 178.4, 137.7, 125.7, 125.1, 122.4, 12;.2, 120.7, 118.5, 109.5, 46.8, 34.0, 32.5, 28.3. LRMS (EI): 231 (M$^+$, 23%), 216 (7%), 172 (100%). HRMS (EI) Calcd. for C$_{14}$H$_{17}$O$_2$N: 231.12593; found: 231.12586.

(i) Preparation of Auxiliary (15)

To a stirred colled (−78° C.) solution of acid (14) (269 mg, 1.16 mol) in THF (20 ml) under argon was added triethylamine (243 μl, 1.75 mmol) and then trimethylacetyl chloride (158 μl, 1.28 mmol), the resulting mixture was warmed to 0° C., stirred for one hour and then re-coiled to −78° C. In a second flask butyllithium (1.27 ml, 1.53M in hexanes, 1.93 mmol) was added drop wise to a stirred cooled (−78° C.) solution of (4S)-(−)-4-isopropyl-2-oxazolidinone (250 mg, 1.94 =mol) in THF (8 ml) under an argon atmosphere, and the resulting lithiated oxazolidinone was added via cannula to the reaction flask. Stirring was continued for one hour and then water (20 ml) was added and the reaction mixture was allows to warm to room temperature whereupon it was extracted with ether (3×30 ml). The combined organic extracts were washed with brine (30 ml) and dried over magnesium sulfate, and concentrates in vacuo. The crude yellow oil was purified by flash column chromatography (40% ether in pet.ether) to afford the desired compound (15) as an off white solid (313 mg, 78%).

IR (CHCl$_3$ soln): 1777, 1693 (s, C=O), 1615, 1540 (w, C=C). $^1$H NMR (400 MHz, CDCl$_3$) δ: 0.67 (3H,d,J=6.9 Hz,CH(CH$_3$)CH$_3$), 0.77 (3H,d, J=6.9 Hz, CH(CH$_3$)CH$_3$), 1.59 (3H,s,CCH$_3$(CH$_3$)), 1.61 (3H,s,CCH$_3$(CH$_3$)), 2.14 (1H, m, CH(CH$_3$)CH$_3$), 3.48 (2H,s,CH$_2$CON), 3.71 (3H,s, NCH$_3$), 3.71 (1H,br,t,J=9.0 Hz, CH$_A$H$_B$O), 3.97 (1H,dd,J=9.0, 2.7 Hz CH$_A$H$_B$O), 4.18 (1H,m,CH($^i$Pr)CH$_2$), 6.86 (1H,s,=CHNH), 7.07 (1H,t,J=8.0 Hz ArH), 7.16 (1H,t,J=8.0 Hz, ArH), 7.24 (1H,d,J=8.0 Hz,ArH), 7.82 (1H,d,J=8.0 Hz ArH). $^{13}$C NMR (75.3 MHz, CDCl$_3$) δ: 171.5, 154.0, 137.5, 125.9, 125.6, 122.1, 121.0, 118.5, 109.3, 62.9, 58.5, 45.4, 35.0, 32.6, 29.6, 28.7, 28.5, 17.9, 14.5. LRMS (EI): 231 (M$^+$, 23%), 216 (7%), 172 (100%).

(j) Preparation of Azide (16)

To a stirred, cooled (−78° C.) solution of oxazolidinone (15) (82.7 mg, 0.242 mmol) in THF (3 ml) under an argon atmosphere was added potassium bis(trimethylsilyl)amide (0.73 ml, 0.4M in THF, 0.29 mmol) and the resulting solution was stirred at −78° C. for one hour. A solution of triisopropylsulfonyl azide (97 mg, 0.315 mmol) in THF (2 ml) precooled to −78° C. was added via cannula and after one minute the reaction was quenched by addition of glacial acetic acid (100 ml), warmed to 40° C. (water bath) and stirred for a further hour. The reaction mixture was then partitioned between dicloromethane (10 ml) and dilute brine (10 ml), and the layers separated. The aqueous phase was extracted with dichloromethane (2×10 ml) and the combined organic extracts washed with sodium hydrogen carbonate (10 ml, sat.aq.), brine (10 ml), dried with magnesium sulfate and concentrated in vacuo. The resulting crude oil was purified by flash column chromatography (30% ether in pet.ether) to afford a mixture of the desired compound (16) and trisiopoylsulphonylamine (56.7 mg total, inseparable, estimated 45 mg of desired compound, approx. 50%).

$^1$H NMR (200 MHz, CDCl$_3$) δ: 0.70 (3H,d,J=6.9 Hz, CH(CH$_3$)CH$_3$), 0.76 (3H, d,J=6.9 Hz, CH(CH$_3$)CH$_3$), 1.62 (3H,s,CCH$_3$,CH$_3$)), 1.66 (3H,s, CCH$_3$(CH$_3$)), 2.16 (1H,m, CH(CH$_3$)CH$_3$) 3.66-3.73 (6H,m,CH$_2$CON, NCH$_3$, CH($^i$Pr)CH$_2$)), 5.66 (1H,s,CHN$_3$), 6.94 (1H,s,=CHNH), 7.06 (1H,t,J=8.0 Hz, ArH), 7.16 (1H,t,J=8.0 Hz,ArH), 7.26 (1H, d,J=8.0 Hz,ArH), 7.75 (1H,d,J=8.0 Hz, ArH).

(k) Preparation of Boc-auxiliary (17)

A mixture of azide (16) (58 mg, semi-crude, <0.152 mmol) 10% palladium on charcoal (30 mg), and di-tert-butyl dicarbonate (66 mg, 0.304 mmol) in ethyl acetate (4 ml) was flushed with argon and then hydrogen and stirred under a hydrogen balloon for sixteen hours at room temperature. The palladium was removed via filtration through celite, the solvent removed in vacuo and the crude mixture purified by flash column chromatography (50% ether in pet.ether) to afford the desired compound (17) (21.8 mg, <50%).

$^1$H NMR (200 MHz, CDCl$_3$) δ: 0.71 (3H,d,J=6.9 Hz,CH(CH$_3$)CH$_3$), 0.73 (3H,d, J=6.9 Hz, CH(CH$_3$)CH$_3$), 1.40 (9H,s, C(CH$_3$)$_3$), 1.53 (3H,s,CCH$_3$(CH$_3$)), 1.59 (3H,s. CCH$_3$(CH$_3$)), 2.10 (1H,m,CH(CH$_3$)CH$_3$), 2.58 (1H,m,CH$_A$H$_B$O), 3.66-3.73 (5H,m, CH$_A$H$_B$O, NCH$_3$, CH($^i$Pr)CH$_2$)), 5.28 (1H, br, NH), 6.03 (1H, br,d,CHNHBoc), 6.98 (1H,s,=CHNH), 7.02 (1H,t,J=8.0 Hz,ArH), 7.16 (1H,t,J=8.0 Hz,ArH), 7.24 (1H,d,J=8.0 Hz,ArH), 7.72 (1H,d,J=8.0 Hz,ArH).

(1) Preparation of Methyl Ester of (17)

To a solution of (17) (13 mg, 0.0285 mmol) in THF (1 ml) and water (0.3 ml) at 0° C. was added lithium hydroxide (8 mg, excess) as a solid in one portion. The resulting suspension was stirred at room temperature for sixteen hours, and then acidified with 1N hydrochloric acid, and the solvent removed in vacuo. The resulting crude white solid was suspended in ether and an ethereal solution of diazomethane added, until the yellow colour of the diazomethane persisted in the reaction mixture and tlc analysis showed complete consumption of starting material. The excess diazomethane was removed under a stream of argon and the remaining solvent removed in vacuo. The resulting crude oil was purified by flash column chromatography (40% ether in pet. ether) to afford the desired compound methyl ester of (17) (7.7 mg. 75%).

$^1$H NMR (400 MHz, CDCl$_3$) δ: 1.38 (9H,s,C(C$\underline{H}_3$)$_3$), 1.47 (3H,s,CCH$_3$(C$\underline{H}_3$)), 1.52 (3H,s,CC$\underline{H}_3$(CH$_3$)), 3.45 (3H,s, CO$_2$C$\underline{H}_3$), 3.72 (3 H, s, NC$\underline{H}_3$), 4.70 (1h, d, br, N$\underline{H}$), 5.05 (1H,d,br,C$\underline{H}$NHBoc), 6.81 (1H,s,=C$\underline{H}$NH), 7.07 (1H,t, J=8.0 Hz Ar$\underline{H}$), 7.21 (1H,t,J=8.0 Hz, Ar$\underline{H}$), 7.30 (1H,d,J=8.0 Hz,Ar$\underline{H}$), 7.80 (1H,d,J=8.0 Hz Ar$\underline{H}$).

(m) Alternative Route to Methyl Ester of (17)

Reversal of the above two steps allows for the synthesis of the same compound in comparable yield.

(n) Preparation of Methylated Methyl Ester

To a suspension of sodium hydride (excess) and methyl iodide (excess) in dry THF (0.5 ml) under an argon atmosphere was added the methyl ester of (17) (10.4 mg 0.0289 mmol) in THF (1 ml) via cannula and the resulting mixture was stirred for sixteen hours at room temperature. Water was added and the mixture was extracted with ether, the combined organic extracts were washed with brine, dried with magnesium sulfate and concentrated in vacuo. The crude oil was purified by flash column chromatography (40% ether in pet.ether) to afford the desired N-methylated methyl ester as a colourless oil (3.1 mg, approx. 30%).

$^1$H NMR (400 MHz, CDCl$_3$) δ: 1.42 (9H,s,C(C$\underline{H}_3$)$_3$), 1.52 (3H,s,CCH$_3$(C$\underline{H}_3$)), 1.64 (3H,s,CC$\underline{H}_3$(CH$_3$)), 2.70 (3H,s, (split) NC$\underline{H}_3$Boc), 3.45 (3H,s, split, CO$_2$C$\underline{H}_3$), 3.71 (3H,s, NC$\underline{H}_3$), 5.40 (1H,s,split, C$\underline{H}$NCH$_3$Boc), 6.98 (1H,s,=C $\underline{H}$NH), 7.00-7.25 (3H,m, Ar$\underline{H}$), 7.72 (1H,d,br,split,Ar$\underline{H}$).

(o) Preparation of (18)

The procedure of step (1) was followed, but the esterification with diazomethane was omitted.

(p) Preparation of (19)

N-Boc-amine acid (18) (10 mmol) and methyl iodide (5 ml; 80 mmol) were dissolved in THF (30 ml) and the solution was cooled to 0° C. under argon. Sodium hydride dispersion (1.32 g; 30 mmol) was added cautiously with gentle stirring. The suspension was stirred at room temperature for 16 h. Ethyl acetate (50 ml) was then added (to consume the sodium hydroxide formed from the excess sodium hydride), followed by water, drop wise, to destroy the excess sodium hydride. The solution was evaporated to dryness, and the oily residue partitioned between ether (30 ml) and water (100 ml). The ether layer was washed with 5% aqueous NaHCO$_3$ (50 ml) and the combined aqueous extracts and acidified to pH 3 with aqueous citric acid. The product was extracted into ethyl acetate (3×25 ml), the extract washed with water (2×25 ml), 5% aqueous sodium thiosulphate (2×25 ml; to remove iodine), and water (2×25 ml), dried over MgSO$_4$ and evaporated to give a pale yellow oil of (19).

3. Coupling of Amino Acids

N-Boc amino acid (19) (1 mmol), amino acid methyl ester of moiety B (1.1 mmol) and coupling agent py-BOP (1.1 mmol) were dissolved in CH$_2$Cl$_2$ (10 ml) under argon. T$\underline{I}$EA (3 mmol) was added and the reaction was stirred for 1 h at room temperature. Excess solvents were removed in vacuo yielding a yellow oily residue which was redissolved in EtOAc (50 ml). Washing the EtOAc solution with 10% citric acid (2×25 ml), water (25 ml), 5% NaHCO$_3$ (2×25 ml), water (25 ml), following -by drying over anhydrous MgSO$_4$ and normal phase silica gel chromatography afforded the protected peptide A-B as a white amorphous solid.

Coupling of the peptide A-B to amino acid moiety of C (5) was carried out in a similar way.

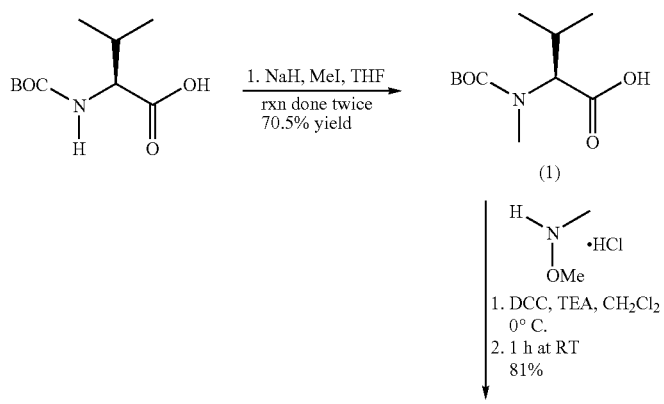

Scheme 1
Synthesis of N—Me-homo vinylogous vaiine ethyl ester (MHVV—OEt)

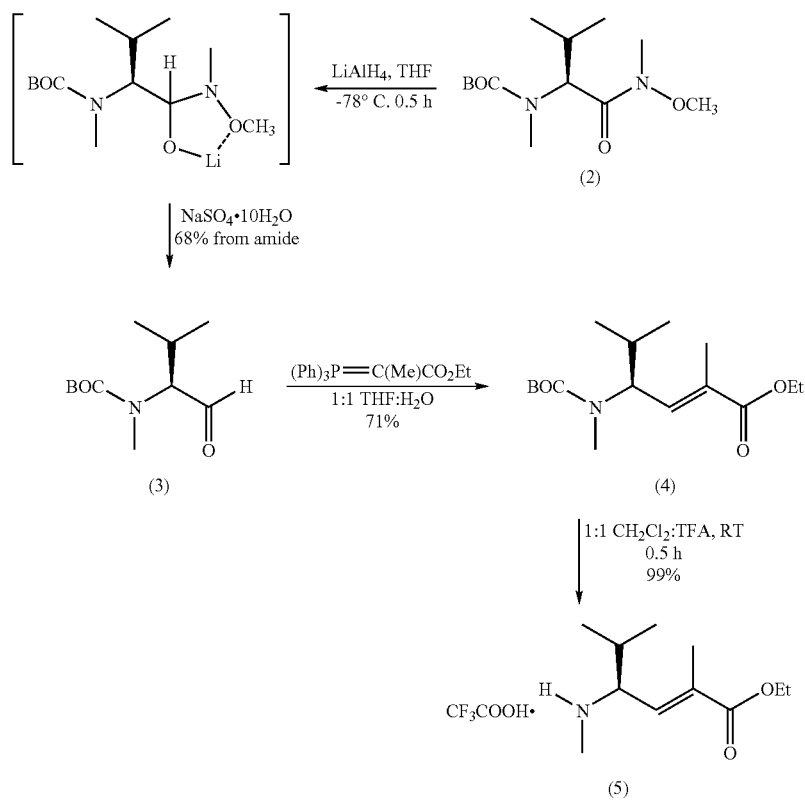
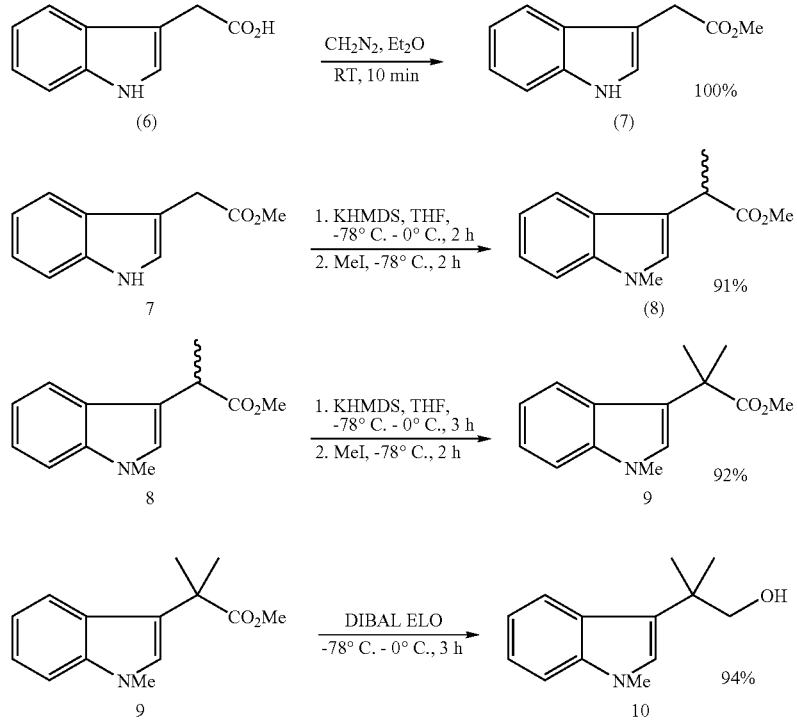

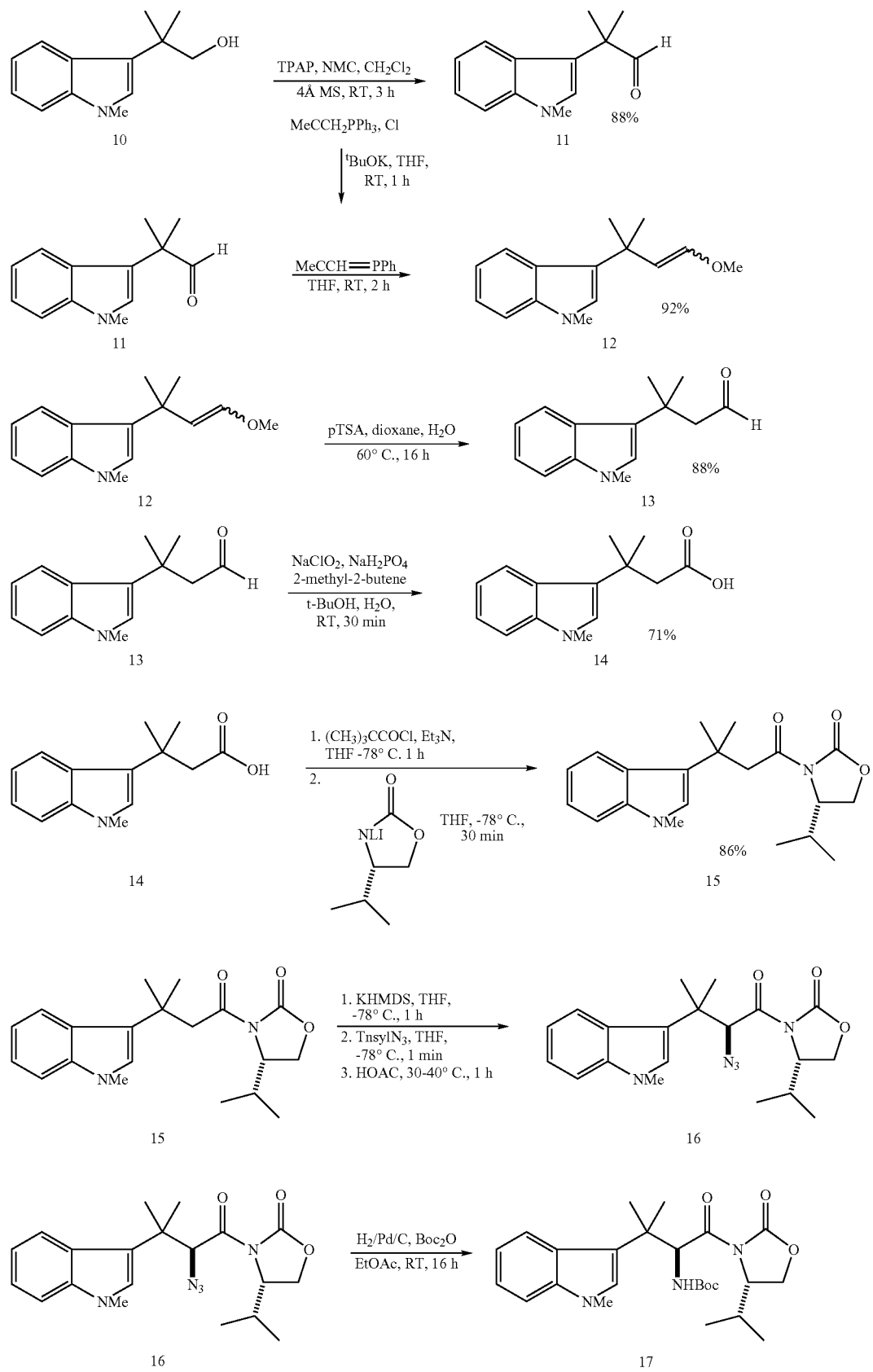

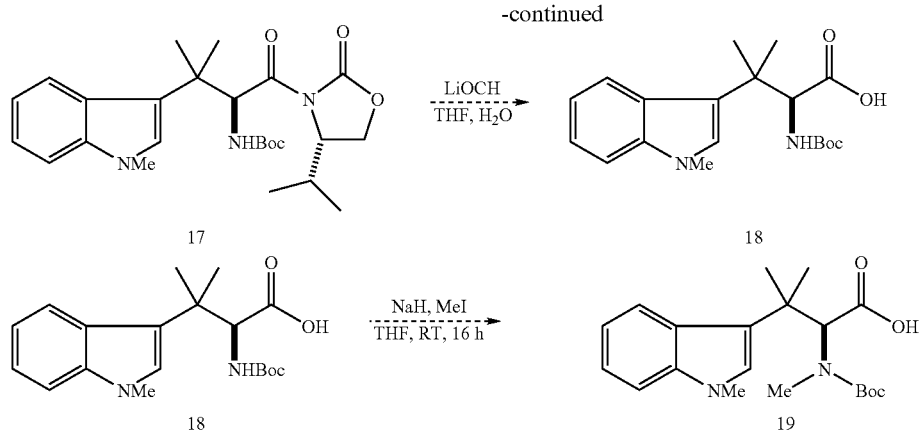

Testing of Compounds

1. The cytotoxicity of compounds described herein have been tested as described in J. Immunol. Methods, 65, 55-63, 1983 and the results are provided in table 4 below, wherein P388, refers to in vitro test versus murine leukaemia P388, U373, refers to in vitro human glioblastoma/astrocytoma U373, HEY refers to in vitro human ovarian carcinoma HEY, MCF7 refers to in vitro human breast cancer MCF7.

2. In in vivo test as described in NIH Publications No. 84-2635, "In Vivo Cancer Models", Developmental Therapeutic Program, Division of Cancer Treatment, National Cancer Institute, Bethesda, Md. hemiasterlin has been found to be cytotoxic. In mice injected with $1 \times 10^6$ P388 leukaemia cells, hemiasterlin resulted in a %TC of 223 after 5 daily doses of 0.45 µg begun 24 hours after implantation. There were several long term survivors in the experiment.

TABLE 4

| compound | $IC_{50}$ Values (µg/ml) | | | | |
|---|---|---|---|---|---|
| | P388 | U373 | HEY | MCF7 | cell mitosis |
| hemiasterlin (Compound A) | $4.57 \times 10^{-5}$ | $1.2 \times 10^{-2}$ | $1.4 \times 10^{-3}$ | $1.58 \times 10^{-4}$ | $1.58 \times 10^{-4}$ |
| hemiasterlin-A (Compound 2) | $1.71 \times 10^{-6}$ | $1.5 \times 10^{-3}$ | $7.6 \times 10^{-3}$ | $1.54 \times 10^{-3}$ | $1.02 \times 10^{-3}$ |
| hemiasterlin-B (Compound 3) | $7.0 \times 10^{-3}$ | | $1.6 \times 10^{-2}$ | $1.50 \times 10^{-2}$ | $9.96 \times 10^{-3}$ |

TABLE 4-continued

| compound | IC$_{50}$ Values (µg/ml) | | | | |
| --- | --- | --- | --- | --- | --- |
| | P388 | U373 | HEY | MCF7 | cell mitosis |
| criamide-B | $7.3 \times 10^{-3}$ | 0.27 | 0.19 | 6.8 | |

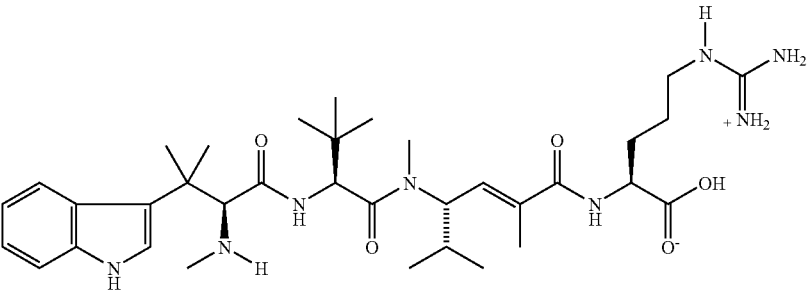

Geodiamolide G (compound I)

| | | 7.7 | 8.6 | | |
| --- | --- | --- | --- | --- | --- | hemiasterlin-OMe

| | | | | $5.4 \times 10^{-3}$ | $2.16 \times 10^{-4}$ |
| --- | --- | --- | --- | --- | --- |

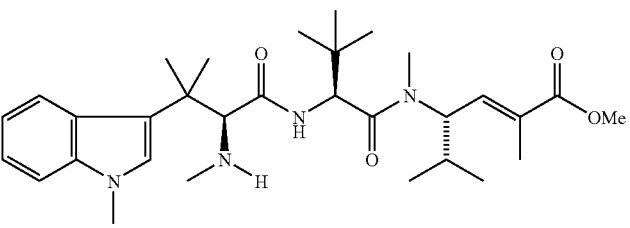

dihydrohemiasterlin

| | | | | | $1.06 \times 10^{-3}$ |
| --- | --- | --- | --- | --- | --- |

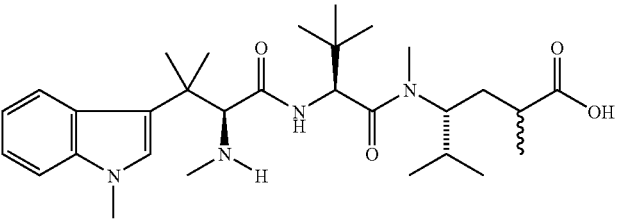

| | | | | | 0.1 |
| --- | --- | --- | --- | --- | --- |

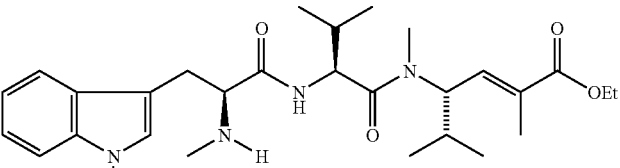

Totally Synthetic analog

3. Compounds described herein were comparatively tested for their antimitotic activity against human mammary carcinoma MCF7 cells.

MCF7 cells were grown as a monolayer in RPMI supplemented with 15% fetal calf serum and antibiotics at 37° C. in humidified 10% CO$_2$. All compounds were dissolved in dimethyl sulfoxide except for vinblastine (a known drug) which was a 1 mg/ml solution in physiological saline. Exponentially growing MCF7 cells were treated with different drug concentrations for 20 h, prepared for chromosome spreads, and the percentage of mitotic cells determined by fluorescence microscopy. The results are shown in FIGS. 1 and 2. Hemiasterlin, Hemiasterlin A and modified compounds were very potent antimitotic agents, with IC$_{50}$ values of 0.3 nM and 3 nM respectively. Hemiasterlin and Hemiasterlin A were more potent than Taxol, Vinblastine and Nocodazole (all known drugs).

The effect of Hemiasterlin and Hemiasterlin A on the morphology of their mitotic spindles was examined by indirect immunofluorescence using a monoclonal antibody to β-tubulin and the distribution of their chromosomes using the fluorescent DNA dye bisbenzimide. In the presence of hemiasterlin A at 2 nM no completely normal spindles were seen. Some cells showed relatively minor abnormalities in which a bipolar spindle was present but the astral microtubules were considerably longer than normal and the chromosomes were not completely confined to the metaphase plate. Most commonly cells had multiple asters, and the chromosomes were distributed in a spherical mass. Half-maximal concentrations of taxol, vinblastine and nocodazole produced the same types of abnormal spindle as hemiasterlin A. Hemiasterlin A at 10 nM, the lowest concentration causing maximal mitotic arrest in MCF7 cells, caused microtubule depolymerisation in mitotic cells. This was also the case for high concentrations of vinblastine and nocodazole. Taxol at high concentrations had a quite different effect, causing bundling of cytoplasmic microtubules in interphase cells and very dense multiple asters in mitotic cells.

These results show that Hemiasterlins cause mitotic arrest and produce abnormal mitotic spindles. They can be used in lieu of other antimitotic drugs in procedures that require blocking cells in mitosis, such as the preparation of mitotic spreads for karyotype analysis. They can also be used to probe microtubule function in mitotic cells.

What is claimed is:

1. A compound of general formula I wherein:

R$_1$, R$_2$, and R$_{70}$ independently represent a hydrogen atom or an optionally substituted alkyl or acyl group, wherein the alkyl or acyl group has up to 8 carbon atoms, and wherein the optional substituents are selected from the group consisting of halogen atoms and nitro, cyano, alkoxy, hydroxy, amino, alkylamino, sulfinyl, alkylsulfinyl, sulfonyl, alkylsulfonyl, amido, alkylamido, alkylcarbonyl, haloalkoxycarbonyl, and haloalkyl groups;

Y represents an optional substituent;

n represents 0, 1, 2, 3, or 4;

R$_3$ represents a hydrogen atom, or an optionally substituted alkyl group;

R$_{74}$ represents a hydrogen atom, a hydroxy group or an optionally substituted alkyl or acyl group;

R$_7$ represents a hydrogen atom or an alkyl group;

R$_{75}$ represents an optionally substituted alkyl group up to 6 carbon atoms; and i) R$_{71}$ represents a hydrogen atom or an optionally substituted alkyl or acyl group; and R$_{72}$ represents a hydrogen atom;

or ii) R$_{71}$ and R$_{72}$ each represent radicals so that a double bond is formed between the carbon atoms to which they are attached.

2. The compound of claim 1, wherein n represents 0.

3. The compound of claim 1, wherein R$_{71}$ represents a hydrogen atom or an alkyl or acyl group.

4. A compound of general formula I wherein:

R$_1$, R$_2$, and R$_{70}$ independently represent a hydrogen atom or an optionally substituted alkyl or acyl group, wherein the alkyl or acyl group has up to 8 carbon atoms, and wherein the optional substituents are selected from the group consisting of halogen atoms and nitro, cyano, alkoxy, hydroxy, amino, alkylamino, sulfinyl, alkylsulfinyl, sulfonyl, alkylsulfonyl, amido, alkylamido, alkylcarbonyl, haloalkoxycarbonyl, and haloalkyl groups;

Y represents an optional substituent;

n represents 0, 1, 2, 3, or 4;

R$_3$ represents a hydrogen atom, or an optionally substituted alkyl group;

R$_{74}$ represents a hydrogen atom, a hydroxy group or an optionally substituted alkyl or acyl group;

R$_7$ represents a hydrogen atom or an alkyl group;

R$_{75}$ represents a group of general formula II:

wherein Q represents an optionally substituted —CH$_2$—, —CH$_2$CH$_2$—, —CH$_2$CH$_2$CH$_2$—, —CH$_2$CHCH—, —CH$_2$C≡C—, or phenylene moiety; and X represents a group —OR$_8$, —SR$_8$, or —NR$_9$R$_{10}$, wherein R$_8$ independently represents a hydrogen atom or an optionally substituted alkyl group, and R$_9$ and R$_{10}$ independently represent a hydrogen atom or an optionally substituted alkyl group having up to 8 carbon atoms; and i) R$_{71}$ represents a hydrogen atom or an optionally substituted alkyl or acyl group; and R$_{72}$ represents a hydrogen atom; or ii) R$_{71}$ and R$_{72}$ each represent radicals so that a double bond is formed between the carbon atoms to which they are attached.

5. The compound of claim 4, wherein X represents a group —OR$_8$, wherein R$_8$ represents a hydrogen atom or a methyl group.

6. The compound of claim 4, wherein X represents a group —NR$_9$R$_{10}$, wherein R$_9$ represents a hydrogen atom or an alkyl group having up to 8 carbon atoms, and R$_{10}$ represents a substituted alkyl group having up to 8 carbon atoms.

7. The compound of claim 1, wherein the compound has antimitotic activity.

8. A compound of general formula I $$\text{(structure I)}$$

wherein
- $R_1$ represents a hydrogen atom;
- $R_2$ represents a hydrogen atom, or an alkyl group, or an acyl group;
- $R_3$ represents a hydrogen atom, or an optionally substituted alkyl group;
- Y represents an optional substituent;
- n represents 0;
- $R_{70}$ and $R_{71}$ independently represent a hydrogen atom or an optionally substituted alkyl group;
- $R_{72}$ and $R_{74}$ represent hydrogen atoms;
- $R_{74}$ represents an optionally substituted alkyl or acyl group;
- $R_7$ represents a hydrogen atom or an alkyl group;
- $R_{75}$ represents a group of general formula III, $$\text{(structure III)}$$

wherein
- $R_4$ represents a hydrogen atom, or an optionally substituted alkyl group;
- $R_5$ represents a hydrogen atom or an alkyl group;
- $R_{76}$ and $R_{77}$ each represent a hydrogen atom or a radical so that a double bond is formed between the carbon atoms to which they are attached; and
- X represents a group —$OR_8$ or a group —$NR_9R_{10}$, wherein
- $R_8$, $R_9$ and $R_{10}$ independently represent a hydrogen atom or an optionally substituted alkyl group.

9. The compound of claim 8, wherein $R_{70}$ and $R_{71}$ each represent a methyl group.

10. A compound of general formula I $$\text{(structure I)}$$

wherein
- $R_1$ represents a hydrogen atom or an alkyl group;
- $R_2$ represents an acyl group;
- $R_3$ represents a hydrogen atom, or an optionally substituted alkyl group;
- Y represents an optional substituent;
- n represents 0;
- $R_{70}$ and $R_{71}$ independently represent a hydrogen atom or an optionally substituted alkyl group;
- $R_{72}$ and $R_{74}$ represent hydrogen atoms;
- $R_{74}$ represents an optionally substituted alkyl or acyl group;
- $R_7$ represents a hydrogen atom or an alkyl group;
- $R_{75}$ represents a group of general formula III, $$\text{(structure III)}$$

wherein
- $R_4$ represents a hydrogen atom, or an optionally substituted alkyl group;
- $R_5$ represents a hydrogen atom or an alkyl group;
- $R_{76}$ and $R_{77}$ each represent a hydrogen atom or a radical so that a double bond is formed between the carbon atoms to which they are attached; and
- X represents a group —$OR_8$ or a group —$NR_9R_{10}$, wherein
- $R_8$, $R_9$ and $R_{10}$ independently represent a hydrogen atom or an optionally substituted alkyl group.

11. The compound of claim 10, wherein $R_{70}$ and $R_{71}$ each represent a methyl group.

* * * * *